United States Patent
Garu et al.

(10) Patent No.: US 9,840,530 B2
(45) Date of Patent: Dec. 12, 2017

(54) MANNOSE-RECEPTOR SELECTIVE LYSINYLATED CATIONIC AMPHIPHILES AND A PROCESS FOR PREPARATION THEREOF

(71) Applicant: COUNCIL OF SCIENTIFIC & INDUSTRIAL RESEARCH, New Delhi (IN)

(72) Inventors: Arup Garu, Hyderabad (IN); Gopikrishna Moku, Hyderabad (IN); Sachin Barad Agawane, Hyderabad (IN); Arabinda Chaudhuri, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 15 days.

(21) Appl. No.: 14/759,144

(22) PCT Filed: Dec. 27, 2013

(86) PCT No.: PCT/IN2013/000806
§ 371 (c)(1),
(2) Date: Jul. 2, 2015

(87) PCT Pub. No.: WO2014/106856
PCT Pub. Date: Jul. 10, 2014

(65) Prior Publication Data
US 2015/0337000 A1    Nov. 26, 2015

(30) Foreign Application Priority Data
Jan. 3, 2013   (IN) .......................... 0017/DEL/2013

(51) Int. Cl.
*A61K 39/00*    (2006.01)
*C07H 15/04*    (2006.01)
*C07C 269/06*    (2006.01)
*A61K 47/18*    (2017.01)
*A61K 47/26*    (2006.01)
*C07C 277/00*    (2006.01)
*A61K 9/127*    (2006.01)
*A61K 31/166*    (2006.01)
*A61K 31/351*    (2006.01)
*A61K 31/7105*    (2006.01)
*A61K 31/711*    (2006.01)
*A61K 45/06*    (2006.01)
*C07C 279/14*    (2006.01)
*C07H 1/00*    (2006.01)
*C07H 13/12*    (2006.01)

(52) U.S. Cl.
CPC .......... *C07H 15/04* (2013.01); *A61K 9/1271* (2013.01); *A61K 31/166* (2013.01); *A61K 31/351* (2013.01); *A61K 31/711* (2013.01); *A61K 31/7105* (2013.01); *A61K 39/00* (2013.01); *A61K 45/06* (2013.01); *A61K 47/186* (2013.01); *A61K 47/26* (2013.01); *C07C 269/06* (2013.01); *C07C 277/00* (2013.01); *C07C 279/14* (2013.01); *C07H 1/00* (2013.01); *C07H 13/12* (2013.01); *C07C 2101/14* (2013.01); *C07C 2101/16* (2013.01)

(58) Field of Classification Search
CPC .............. A61K 2300/00; A61K 31/166; A61K 31/351; A61K 31/7105; A61K 31/711; A61K 2800/26; A61K 2800/592; A61K 2800/622; A61K 2800/651; A61K 39/00; A61K 45/06; A61K 47/186; A61K 47/26; A61K 8/0241
USPC ..... 435/375, 455, 458; 424/184.1; 536/17.9; 564/152
See application file for complete search history.

(56) References Cited

FOREIGN PATENT DOCUMENTS

WO   WO2008/001166   1/2008
WO   WO2009/109996   9/2009
WO   WO2012/035557   3/2012

OTHER PUBLICATIONS

Srinivas, R. et al.: "A Long-lasting Dendritic Cell DNA Vaccination System Using Lysinylated Amphiphiles With Mannose-mimicking Head-groups", Biomaterials, vol. 33, (2012), pp. 6220-6229.
Srinivas, R. et al.: "Cationic Amphiphiles: Promising Carriers of Genetic Materials in Gene Therapy", Chem. Soc. Rev., vol. 38, (2009), pp. 3326-3338.
Srinivas, R. et al.: "Cationic Amphiphiles with Shikimic Acid Headgroup Shows More Systemic Promise Than Its Monnosyl Analogue as DNA Vaccine Carrier in Dendritic Cell Based Genetic Immunization", Journal of Medicinal Chemistry, vol. 53, No. 3, (2010), pp. 1387-1391.

*Primary Examiner* — Janet L Epps-Smith
(74) *Attorney, Agent, or Firm* — Norton Rose Fulbright US LLP

(57) ABSTRACT

The present invention relates to the mannose-receptor selective lysinylated cationic amphiphile and a process for preparation thereof. The compounds of the present invention can target DNA vaccines to antigen presenting cells (APCs) such as macrophages and dendritic cells (DCs), via mannose receptors expressed on the cell surface of APCs. The cationic amphiphiles disclosed herein show enhanced cellular and humoral immune response compared to their mannosyl counterparts in genetic immunization in mice. The present invention discloses that immunization with electrostatic complexes (lipoplexes) of DNA vaccines encoding melanoma antigens (gp100 and tyrosinase) and liposome of the presently described novel lysinylated cationic amphiphiles with mannose-mimicking shikimoyl head-groups provides long-lasting (100 days post melanoma tumor challenge) protective immunity in all immunized mice. Cationic amphiphiles with mannose-mimicking shikimoyl head-groups described in the present invention are likely to find future applications in the field of genetic immunization.

19 Claims, 7 Drawing Sheets

Scheme 1: Synthesis of Lipid (X) with mannose mimicking Shikimic Acid Head Group:

Reagents: i) EDCI, HOBt, DIPEA and DCM; ii) Pd(OH)$_2$-C, MeOH,EtOAc, H$_2$; iii)EDCI, HOBt, DIPEA and DCM; iv)TFA, DCM,0°C; v) Di-Boc-thiourea, Et$_3$N, HgCl$_2$; vi) CH$_3$I, DCM; vii) MeOH, K$_2$CO$_3$,Amberlite IRP64 for H$^+$ion exchnge; viii) TFA, DCM,0°C; ix) Amberlyst A-26 resin for Cl$^-$ ion exchange;

MANNOSE-RECEPTOR SELECTIVE LYSINYLATED CATIONIC AMPHIPHILES AND A PROCESS FOR PREPARATION THEREOF

CROSS-REFERENCE TO RELATED APPLICATIONS

This application is a national phase application under 35 U.S.C. §371 of International Application No. PCT/IN2013/000806 filed 27 Dec. 2013, which claims priority to Indian Patent Application No. 0017/DEL/2013 filed 3 Jan. 2013. The entire contents of each of the above-referenced disclosures is specifically incorporated herein by reference without disclaimer.

FIELD OF THE INVENTION

The present invention relates to the mannose-receptor selective lysinylated cationic amphiphiles useful for genetic immunization. The present invention particularly relates to the novel series of lysinylated cationic amphiphiles containing both guanidine as well as mannose-mimicking shikimoyl, quinoyl and mannosyl head-groups. The present invention further relates to the process for preparation mannose-receptor selective lysinylated cationic amphiphiles. The present invention also relates to the liposomal formulations of the cationic amphiphiles capable of targeting DNA vaccines to antigen presenting cells (APCs) in genetic immunization.

BACKGROUND OF THE INVENTION

DNA vaccination, the administration of antigen encoded DNA, is gaining increasing attention as an emerging therapeutic approach for the treatment of many complex disorders including cancer, infectious disease, and allergies (Ishii, K. J. et al. Nature 2008; 451:725-729, Rice, J. et al. Nat. Rev. Cancer. 2008; 8:108-120). DNA vaccines are capable of inducing both humoral and cellular immune responses and are regarded as potentially safer than their attenuated virus counterparts (Gurunathan, S. et al. Annu. Rev. Immunol. 2000; 18:927-974, Liu, M. A. J. Int. Med. 2003; 253:402-410). However, clinical trials have revealed that the immune response induced by a topical injection of naked DNA is insufficient (Roy, M. J. et al. Vaccine, 2000; 19:764-778, Rosenberg, S. A. et al. Hum. Gene Ther. 2003; 14:709-714). Studies have shown that transfection and subsequent activation of antigen presenting cells (APCs) such as dendritic cells (DC) and macrophages are key events in the development of immunity following genetic immunization (Akbari, O. et al. J. Exp. Med. 1999; 189:169-178, Chattergon, M. A. et al. J. Immunol. 1998; 160: 5707-5718). Mountain and co-workers demonstrated that immunization of mice with monocyte-derived dendritic cells transfected with a complex of cationic peptide and a gene encoding tumor associated antigens protected the mice from a lethal challenge with melanoma cells (Irvine, A. S. et al. Nat. Biotechnol. 2000; 18:1273-1278).

Antigen presenting cells such as dendritic cells and macrophages process the antigenic protein through their proteasome complexes into small peptide fragments. These small peptide fragments are then presented to the immune cells (CD8+ and CD4+ T cells) via MHC class I and MHC class II molecules resulting in the induction of cytotoxic T lymphocyte (CTL) and humoral responses (Steinman, R. M. Annu. Rev. Immunol. 1991; 9: 271-296, Banchereau, R. M. and Steinman, R. M. Nature 1998; 392:245-252, Germain, R. N. Cell 1994; 76:287-299, Akbari, O. et al. J. Exp. Med. 1999; 189:169-178, Chattergon, M. A. et al. J. Immunol. 1998; 160:5707-5718, Banchereau, J. and Steinman, R. M. Nature 1998; 392: 245-252). However, antigen presenting cells are hard to transfect. Use of cationic microparticles (Hedley, M. L. et al. Nat. Med. 1998; 4:365-368; Singh, M. et al. Proc. Natl. Acad. Sci. USA 2000; 97:811-816), cationic liposomes (Perrie, Y. et al. Vaccine 2001; 19:3301-3310), and cationic peptide (Irvine, A. S. et al. Nat Biotechnol 2000; 18:1273-1278), etc. have previously been reported for transfection of APCs in ex-vivo. Attempts have been made to increase the potency of immune response through direct transfection of APCs by delivering the antigen encoding DNA via cationic liposomes (Gregoriadis, G. et al. FEBS Lett. 1997; 402:107-110, Klavinskis, L. S. et al. Vaccine 1997; 15: 818-820, Perrie, Y. et al. Vaccine 2001; 19:3301-3310, Hattori, y. et al. Biochem. Biophys. Res. Comm. 2004; 317:992-999). Cationic liposomes owing to their non-toxic and bio-compatible nature offer great advantage over other means of DNA delivery.

A promising approach for enhancing the efficacy of DNA vaccination is based on targeting DNA vaccines to APCs via mannose receptor, a 180 kDa multi-domains unique transmembrane receptors expressed on their cell surfaces (Sallusto, F. et al. J. Exp. Med. 1995; 182:389-400). Previously Srinivas, R. et al. demonstrated that cationic amphiphiles with mannose-mimicking quinic and shikimic acid head-groups can target DNA to antigen presenting cells via mannose receptors (Srinivas, R. et al. J. Med. Chem. 2010; 53:1387-1391). In the same work it was demonstrated that immunization with autologous DCs pre-transfected with electrostatic complexes (lipoplexes) of a plasmid DNA encoding melanoma tumor associated antigen (MART1) and liposomes of two novel amphiphiles with mannose-mimicking quinic and shikimic acid head-groups provides significant protective immunity against lethal melanoma tumor challenge in immunized syngeneic mice (Srinivas, R. et al. J. Med. Chem. 2010; 53:1387-1391). More recently, Srinivas, R. et al. has developed mannose receptor specific lysinylated cationic amphiphiles with mannose-mimicking shikimic and quinic acid head-groups for use in dendritic cell based genetic immunization (Srinivas, R. et al. Indian Patent Application. No. 2170/DEL/2010). However, there a number of time-consuming and cost-ineffective steps to be followed in dendritic cell based genetic immunization processes. One needs to painstakingly isolate the autologous dendritic cells (DCs) from the recipients. The isolated DCs then needs to be ex vivo (outside the body) transfected with DNA vaccines of interest and finally the ex-vivo transfected DCs needs to be re-implanted back into recipient body. Stated differently, the currently practiced ex vivo dendritic cell transfection based genetic immunization procedures are labor-intensive and are likely to be prohibitibly costly for large scale applications. To this end, using electroporation technique for delivering DNA, Steinman and coworkers succeeded in enhancing the efficacy of genetic immunization by targeting DNA vaccines to DCs under in-vivo settings. Their approach is based on construction of DNA vaccine encoding antigenic protein and a single-chain Fv antibody (scFv) specific for the DC-restricted antigen-uptake receptor DEC205 (Nchinda, G. et al. J. Clin. Invest. 2008; 118:1427-1436; Nchinda, G. et al. Proc. Natl Acad. Sci. USA. 2010; 107: 4281). However, large scale construction of such DNA vaccines encoding both antigenic proteins and scFv is unlikely to be cost-effective. More recently Hashida and coworkers reported development of mannose-receptor selective and ultrasound-responsive mannosylated liposomes for in vivo transduction of DCs in genetic immunization (Un K. et al. Biomaterials 2010; 31: 7813-7826; Un K. et al. Mol Pharm 2011; 8: 543-554).

Using p-CMV-β-gal (encoding β-galactosidase enzyme) as a model DNA vaccine, the present invention discloses that direct in vivo administration (i.e. without the need of isolating autologous DCs) of the electrostatic complexes of p-CMV-β-gal and liposomes of the presently described mannose-receptor selective lysinylated cationic amphiphiles containing both guanidine and mannose-mimicking shikimoyl head-groups in mice are highly efficient in eliciting both cellular and humoral immune responses against β-gal antigen. This invention also discloses the applications of the presently described lysinylated cationic amphiphiles with both guanidine and mannose-mimicking shikimoyl headgroup in genetic immunization using DNA vaccines encoding Gp100 and tyrosinase, two human melanocyte lineage-specific antigens expressed by majority of human malignant melanoma (Coulie P. G. et al. J Exp Med 1994; 180: 35-42; Kawakami Y. et al. Proc Natl Acad Sci USA 1994; 91: 3515-9; Topalian S. L. et al. Proc Natl Acad Sci USA. 1994; 91: 9461-9465; Brichard V. et al. J. Exp Med. 1993; 178: 489-95). These antigens share 77% & 82% amino-acid sequence identities, respectively, with their murine counterparts (Zhai Y et al. J Immunother 1997; 20: 15-25; Colella A. T. et al. J. Exp Med. 2000; 191: 1221-1231). The present invention discloses that direct in vivo immunization with electrostatic complexes (lipoplexes) of DNA vaccines p-CMV-gp100 and p-CMV-tyrosinase (encoding melanoma antigens gp-100 & tyrosinase, respectively) and liposome of the presently described lysinylated cationic amphiphiles with both guanidine and mannose-mimicking shikimic acid head-groups provides long-lasting (100 days post tumor challenge) tumor protection against aggressive melanoma tumor challenge in immunized mice. The presently described simple non-viral in vivo DC-targating system may find future exploitations in inducing long-lasting immune response in genetic immunization.

OBJECT OF THE INVENTION

The main object of the present invention is to provide novel lysinylated cationic amphiphiles containing guanidine as well as mannose-mimicking shikimic and quinic acid head-groups for efficient delivery of genetic materials into antigen presenting cells and the methods of their preparation.

Still another object of the present invention is to show that the cellular uptake of the complex of liposomes of the presently described cationic amphiphiles and model DNA vaccine is mediated by the mannose receptors of the antigen presenting cells.

Yet another object of the present invention is to show that the complex of the liposomes prepared with the presently described cationic amphiphiles with mannose-mimicking head-groups and the model DNA vaccine elicit enhanced cellular and humoral immune responses compared to those elicited by the lipoplexes prepared from liposomes of the corresponding cationic amphiphiles with mannosyl head-groups.

Still another of the present invention is to show that direct in vivo immunization of mice with the complex of the liposomes prepared with the presently described cationic amphiphiles with guanidine and mannose-mimicking shikimoyl head-groups and DNA vaccine encoding gp100 and tyrosinase melanoma antigens can induce long lasting anti-tumor (melanoma) immune responses in immunized mice.

SUMMARY OF THE INVENTION

Accordingly the present invention relates to the cationic amphiphile compounds of formula I

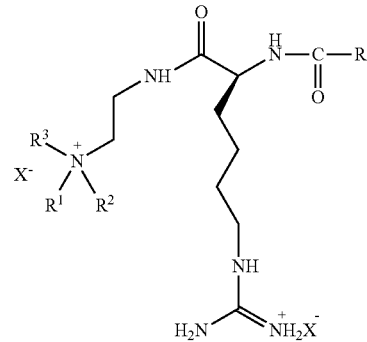

wherein, R is selected from the group consisting of shikimoyl, quinoyl, and mannosyl group;

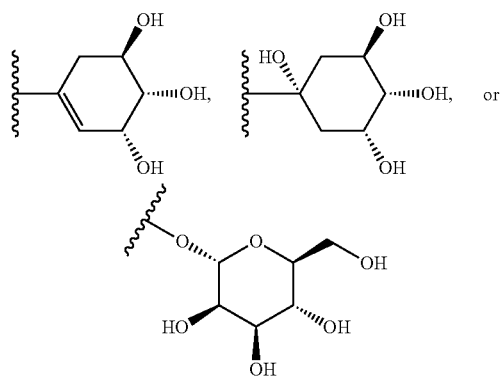

$R^1$ and $R^2$ is independently hydrogen or a lipophilic moiety and $R^1$ and $R^2$ are not hydrogen at the same time;

$R^3$ is independently hydrogen, $C_1$-$C_5$ alkyl, $C_1$-$C_5$ hydroxy and $C_1$-$C_5$ amino;

X is optionally selected from chlorine or bromine;

wherein lipophilic moiety is selected from the group consisting of $C_{8-24}$ alkyl, mono-, di- and tri-unsaturated alkenyl.

In an embodiment of the present invention, the compound is selected from the group consisting of:

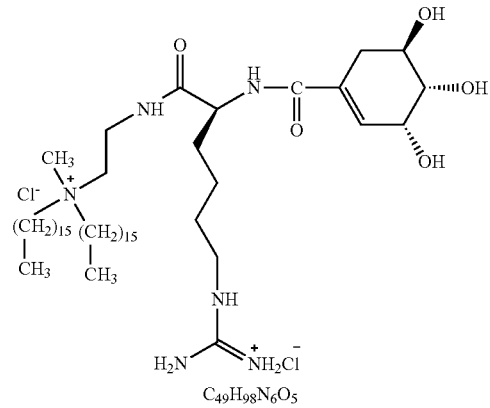

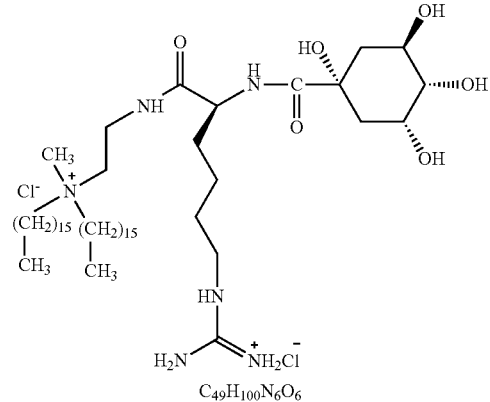

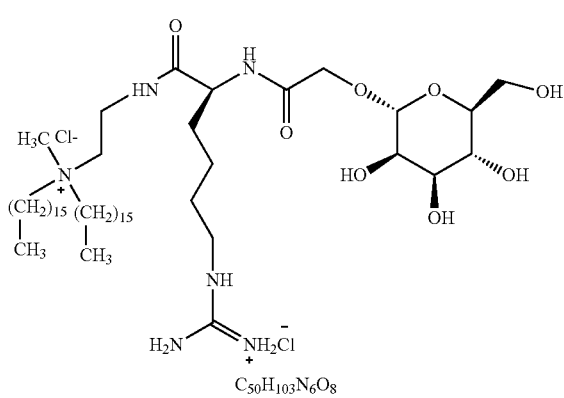

In still another embodiment of the present invention, said compound is used for in vivo delivery of DNA vaccine.

In still another embodiment of the present invention, a process for the preparation of compound of formula I, said process comprises of following steps:
(a) coupling of compound of formula II with L-lysine derivatives in polar aprotic solvent to obtain compound of formula III, followed by acid deprotection to obtain compound of formula IV;
(b) coupling of compound of formula IV, obtained from step (a) with shikimic acid, quinic acid or mannose to obtain the compound of formula V;
(c) deprotecting compound of formula V obtained from step (b) to obtain compound of formula VI followed by guanidinylation of compound of formula VI in aprotic solvent to obtain compound of formula VII;
(d) quaternization of the compound of formula VII obtained from step (c) with methyl iodide to obtain compound of formula VIII followed by base mediated deprotection in polar protic solvent to obtain compound of formula IX and finally extraction to obtain compound of formula I.

In yet another embodiment of the present invention, the compound of formula II is having 8-24 carbon atoms.

In still another embodiment of the present invention, the polar aprotic solvent is selected from the group consisting of dichloromethane, dimethyl formamide, dimethylsulphoxide, pyridine and triethyl amine.

In yet another embodiment of the present invention, the base is selected from the group consisting of potassium carbonate, lithium hydroxide, sodium hydroxide, sodium carbonate, potassium hydroxide, sodium methoxide and potassium methoxide.

In still another embodiment of the present invention, the polar protic solvent for base mediated deprotection is selected from the group comprising methanol, ethanol and mixture of water & methanol.

In still another embodiment of the present invention, a formulation comprising the cationic amphiphiles compound of formula I, a co-lipid, and a polyanionic compound along with physiologically acceptable additive.

In yet another embodiment of the present invention, the formulation further comprises helper lipids.

In still another embodiment of the present invention, the co lipid is selected from the group consisting of phosphatidylethanolamine, phosphatidylphosphocholine, neutral phosphatidyl ethanolamine or, neutral phosphatidyl choline, phosphatidylglycerol, cholesterol, 1,2-syn-dioleoyl-glycerolphosphatidylethanolamine (DOPE) and cholesterol.

In yet another embodiment of the present invention, the molar ratio of the cationic amphiphile to colipid used in formulation is in the range of 1:1 to 3:1.

In still another embodiment of the present invention, the preferred molar ratio of cationic amphiphile to colipid in formulation is 1:1.

In yet another embodiment of the present invention, a polyanionic compound used in formulation, is selected from the group consisting of nucleic acid, protein, an oligonucleotide, a peptide, a protein and a drug.

In still another embodiment of the present invention, the nucleic acid is selected from the group consisting of plasmid, a ribonucleic acid, a ribosomal RNA, antisense polynucleotide of RNA or DNA, polynucleotide of genomic DNA, cDNA and mRNA.

In yet another embodiment of the present invention, the formulation is administered via cutaneous, sub-cutaneous, intradermal, nasal, intravenous, intramuscular, intraperitonial or pulmonary route.

In still another embodiment of the present invention, the formulation is administered intracellularly in the range of 25 to 100 microliters.

In yet another embodiment of the present invention, the formulation is administered to cells at a ratio ranging from 0.1 to 0.5 microgram of DNA to 50,000 cells.

In still another embodiment of the present invention, the cationic amphiphiles in the formulation ranges from 9.0 to 0.3 microgram and lipid to DNA charge ratios ranges from 0.3:1 to 9:1.

In yet another embodiment of the present invention, the formulation transfects antigen presenting cells under both invitro as well as invivo settings.

In still another embodiment of the present invention, the formulation transfects mbmDCs more efficiently than the commercially available transfecting reagent Lipofectamine 2000.

In yet another embodiment of the present invention, the formulation induces both cellular and humoral immune response.

In still another embodiment of the present invention, the formulation exhibits long lasting protection against any disease in human or animal body using suitable known immunogen.

In yet another embodiment of the present invention, a method for inducing immune response, the method comprising administering the formulation comprising the cationic amphiphiles compound of formula I, a co-lipid, and a polyanionic compound along with physiologically acceptable additive.

In yet another embodiment of the present invention, a method for producing immune response, the method comprising: administering the formulation, with a polynucleotide wherein said polynucleotide encodes an immunogen to at least one mouse thereby generating at least one immunized mouse.

An important embodiment of the invention is evaluation of mannose-receptor selective efficiencies of these new cationic amphiphiles in delivering genes into antigen presenting cells.

Another important embodiment of the invention is evaluation of both cellular and humoral immune responses elicited by the presently disclosed formulations in mice.

Most important embodiment of the invention is evaluation of long-lasting (100 days post tumor challenge) tumor protection against aggressive melanoma tumor in syngeneic mice immunized with electrostatic complexes (lipoplexes) of a plasmid DNA encoding melanoma tumor associated antigens (gp-100 & tyrosinase) and liposomes of novel lysinylated cationic amphiphiles with mannose-mimicking shikimoyl head-groups.

DETAILED DESCRIPTION OF THE INVENTION

Figure 1:
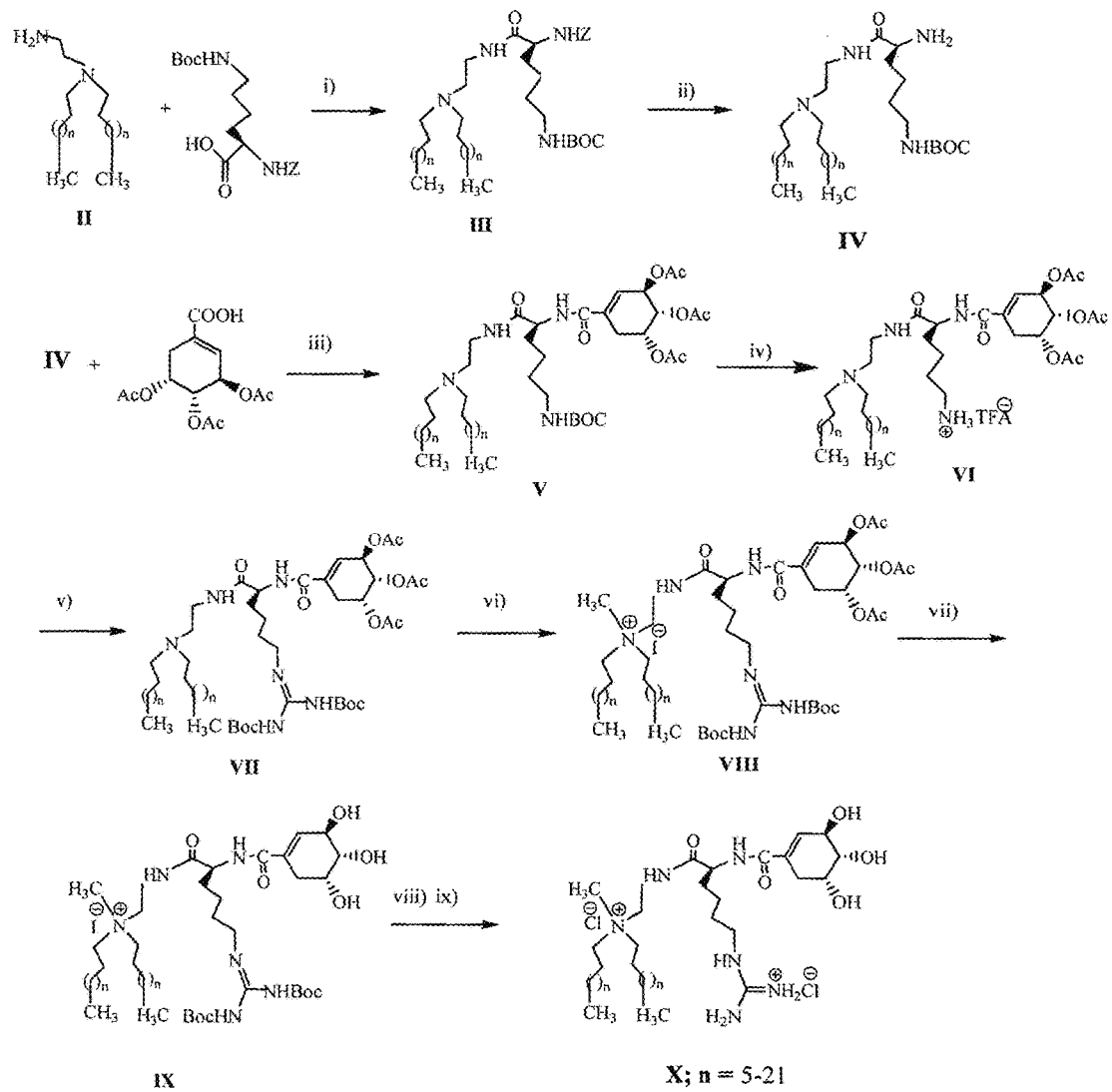
FIG. 1 (Scheme 1) is a schematic representation of the synthetic procedures used for the preparation of cationic amphiphiles containing mannose-mimicking shikimoyl head-groups.

The present invention provides the mannose-receptor selective lysinylated cationic amphiphiles and a process for preparation thereof.

The present invention further relates to a series of novel lysinylated cationic amphiphiles compound of formula I containing both guanidine as well as mannose-mimicking shikimoyl and quinoyl head-groups and processes for their synthesis, evaluation of their mannose receptor specific gene transfer properties in antigen presenting cells and evaluation of both cellular and humoral immune responses in mice elicited by subcutaneous administration of the complex of the liposomes prepared with the presently described cationic amphiphiles and a model DNA vaccine.

The present invention also discloses that cationic amphiphile containing mannose-mimicking shikimoyl-head-group is more efficacious in eliciting both cellular and humoral immune responses than the corresponding cationic amphiphiles with mannosyl head groups as well as cationic amphiphile containing mannose-mimicking quinoyl-head-groups region in dendritic cell based genetic immunization in mice. Most importantly, here we show that subcutaneous immunization of mice with electrostatic complexes (lipoplexes) of a plasmid DNA encoding melanoma tumor associated antigens (gp100 and tyrosinase) and liposomes of novel lysinylated cationic amphiphiles with mannose-mimicking shikimoyl head-groups provides long-lasting (100 days post tumor challenge) tumor protection against aggressive melanoma tumor in immunized mice.

Mannose receptor is a 180 kDa transmembrane protein consisting of five domains: a cystine rich amino terminus, a fibronectin type II repeat region, eight carbohydrate recognition domains (CRD), a transmembrane domain and a cytoplasmic domain. The mannose receptor selectively binds to molecules or micro-organisms carrying sugars such as mannose, fucose, N-acetylglucosamine and glucose on their surface through the eight CRD domains (Apostolopoulos, V. et al. Curr. Mol. Med. 2001; 1: 469-474). A major contribution to the binding is provided by the extensive network of hydrogen bonds and coordination bonds between two equatorial, vicinal hydroxyl groups (at positions 3 & 4) in D-mannose, a calcium ion, two asparagines and two glutamic acid residue of the receptor protein (Weis, W. I. et al. Nature 1992; 360:127-134, Drickamer, K. Nature 1992; 360:183-186). Thus, the mannose receptor plays a key role in imparting protective immunity against a host of antigenic micro-organisms expressing mannose on their cell wall. Since both dendritic cells and macrophages (antigen presenting cells, APCs) predominantly express endocytic mannose receptors on their cell surfaces (Apostolopoulos, V. et al. Curr. Mol. Med. 2001; 1:469-474), the selective uptake of cationic lipid:DNA complexes (lipoplexes) by the APCs should, in principle, be enhanced by the covalent modification of the liposomal surface with APC specific ligands.

A promising approach for enhancing the efficacy of DNA vaccination is based on targeting DNA vaccines to APCs via mannose receptor, a 180 kDa multi-domains unique transmembrane receptors expressed on their cell surfaces (Sallusto, F. et al. J. Exp. Med. 1995; 182:389-400). Using p-CMV-β-gal (encoding β-galactosidase enzyme) as a model DNA vaccine, the present invention discloses that direct in vivo administration (i.e. without the need of isolating autologous DCs) of the electrostatic complexes of p-CMV-β-gal and liposomes of the presently described mannose-receptor selective lysinylated cationic amphiphiles containing both guanidine and mannose-mimicking shikimoyl head-groups in mice are highly efficient in eliciting both cellular and humoral immune responses against β-gal antigen. This invention also discloses the applications of the presently described lysinylated cationic amphiphiles with both guanidine and mannose-mimicking shikimoyl head-group in genetic immunization using DNA vaccines encoding Gp100 and tyrosinase, two human melanocyte lineage-specific antigens expressed by majority of human malignant melanoma (Coulie P. G. et al. J Exp Med 1994; 180: 35-42; Kawakami Y. et al. Proc Natl Acad Sci USA 1994; 91: 3515-9; Topalian S. L. et al. Proc Natl Acad Sci USA. 1994; 91: 9461-9465; Brichard V. et al. J. Exp Med. 1993; 178: 489-95). These antigens share 77% & 82% amino-acid sequence identities, respectively, with their murine counterparts (Zhai Y et al. J Immunother 1997; 20: 15-25; Colella A. T. et al. J. Exp Med. 2000; 191: 1221-1231). The present invention discloses that direct in vivo immunization with electrostatic complexes (lipoplexes) of DNA vaccines p-CMV-gp100 and p-CMV-tyrosinase (encoding melanoma antigens gp-100 & tyrosinase, respectively) and liposome of the presently described lysinylated cationic amphiphiles with both guanidine and mannose-mimicking shikimic acid head-groups provides long-lasting (100 days post tumor challenge) tumor protection against aggressive melanoma tumor challenge in immunized mice. The presently described simple non-viral in vivo DC-targating system may find future exploitations in inducing long-lasting immune response in genetic immunization. The present invention also relates to processes for the preparations of the said novel series of cationic amphiphiles with mannose-mimicking head-groups as well as the synthetic processes for their mannosyled analog. In addition, the present invention also discloses the mannose receptor mediated gene transfer properties of the presently disclosed cationic amphiphiles in antigen presenting cells (APCs) mouse bone marrow derived dendritic cells (mbmDCs). The novel cationic amphiphiles containing mannose-mimicking shikimic and quinic acid head-groups are potentially useful to deliver genetic materials encoding therapeutic antigens to antigen presenting cells which over express mannose receptors.

The distinctive novel structural features common to the cationic amphiphiles with mannose-mimicking head-groups disclosed in the present invention include: (1) The presence of hydrophobic groups which are directly linked to the positively charged nitrogen atom; (2) the presence of mannose receptor binding polar quinic acid head-groups covalently linked to the positively charged quaternized nitrogen atoms through lysine functionality and (3) the presence of guanidine head group is directly linked to the lysine side chain amino group. It is believed that these unique structural features contribute significantly to the mannose receptor mediated gene transfer efficiencies of the presently disclosed cationic amphiphiles containing mannose-mimicking head-groups. The area of science that is likely to be benefited most from the present invention is the field of genetic immunization or DNA vaccination. According to the practice of the present invention, "cationic" means the positive charge is either on quaternized nitrogen or on a protonated nitrogen atom. The cationic characters of the present amphiphiles may contribute to the enhanced interaction of the amphiphiles with biologically active molecules such as nucleic acids and/or with cell constituents such as plasma membrane glycoproteins. Such enhanced interaction between the cationic amphiphiles and therapeutically active biological macromolecules and/or cell membrane constituents may play a key role in successfully transporting the therapeutic molecules into the cells.

The lipids of the present invention with mannose-mimicking shikimoyl and quinoyl head-groups have certain common structural and functional groups. As such, said cationic amphiphiles are represented by the following formula I:

Formula I

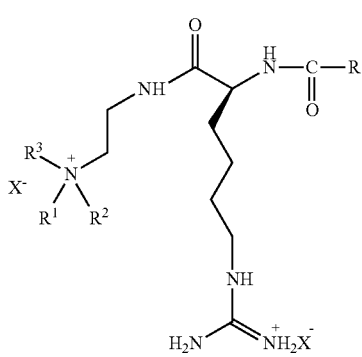

Wherein, R is selected from the group consisting of shikimoyl, quinoyl, and mannosyl group, $R^1$ and $R^2$ are each independently hydrogen or a lipophilic moiety and $R^1$ and $R^2$ are not hydrogen at the same time;

$R^3$ is independently hydrogen or $C_1$-$C_5$ alkyl $C_1$-$C_5$ hydroxy and $C_1$-$C_5$ amino; the guanidine head group is directly linked to the side chain amino group of lysine X is optionally selected from chlorine or bromine wherein lipophilic moiety is selected from the group consisting of $C_{8-24}$ alkyl, mono-, di- and tri-unsaturated alkenyl.

In a preferred embodiment of the present invention, the disclosed cationic lipid is cationic amphiphile 1 wherein $R^1$=$R^2$=n-hexadecyl, $R^3$=methyl and $X^-$ is a chloride and shikimoyl group is the mannose-mimicking head-group.

In another second preferred embodiment of the present invention, the disclosed cationic lipid is cationic amphiphile 2 wherein $R^1$=$R^2$=n-hexadecyl, $R^3$=methyl and $X^-$ is a chloride ion and quinic acid is the mannose-mimicking head-group.

In another preferred embodiment of the present invention, the disclosed cationic lipid is cationic amphiphile 3 wherein $R^1$=$R^2$=n-hexadecyl, $R^3$=methyl and $X^-$ is a chloride ion and mannose is the mannose-mimicking head-group.

The cationic amphiphiles of the present invention have a lipophilic domain that facilitates the formation of lipid complexes or aggregates in aqueous solutions. The lipophilicity of the hydrophobic domains and the hydrophilicity of the polar quinic acid head-group domains are such that when the cationic lipids are confronted with aqueous solutions, lipid aggregates are formed in the presence or absence of a second compound. Exemplary lipophilic $R_1$ and $R_2$ groups include (1) saturated $C_8$-$C_{24}$ alkyl groups and (2) unsaturated $C_8$-$C_{24}$ alkenyl groups containing 1, 2, or 3 double bonds.

Synthetic strategies employed for preparing the presently described cationic amphiphiles with mannose-mimicking shikimoyl head-groups (X) are depicted below schematically in Schemes 1. Cationic amphiphiles with Shikimoyl head-groups (X, Scheme 1) were synthesized by peptide coupling of the starting mixed tertiary-primary amine (compound of formula II) shown in Scheme 1 (prepared by reacting N,N-di-n-tetradecylamine with N-tert-butyloxycarbonyl protected 2-bromoethylamine in ethyl acetate in presence of anhydrous potassium carbonate followed by deprotection and neutralization as reported earlier by Kumar, V. V. et al. in Gene. Ther. 2003; 10:1206-1215) with appropriately protected lysine derivative (containing protected side-chain and protected alpha-amine groups). The coupled product (intermediate III, Scheme 1) was deprotected and the resulting amino compound (intermediate IV, Scheme 1) upon peptide coupling with tri-O-acetyl shikimic acid derivative afforded the intermediateV (Scheme 1). The coupled product (intermediate V, Scheme 1) was deprotected and the resulting amino compound (intermediateVI, Scheme 1) upon coupling with Di-Boc-Thiourea in presence of mercuric chloride afforded the intermediate VII (Scheme 1) The intermediate VII upon quaternization with huge excess of methyl iodide provided the quaternized intermediate VIII (Scheme 1) which upon reaction with methanolic sodium methoxide followed by chloride ion exchange over Amberlyst A-26 Chloride ion exchange resin afforded the target cationic amphiphiles X (Scheme 1). Details of synthetic procedures for cationic amphiphiles X with shikimic acid head-groups are described below in Example 1 for synthesis of cationic amphiphile 1 (as a representative example). Same synthetic strategies were employed for preparing cationic amphiphiles with mannose-mimicking quinic acid head-groups (Y, Scheme 2) as were adopted for syntheses of cationic amphiphiles X with shikimic acid head-groups (Scheme 1) except using O-tetraaceyl derivative of quinic acid instead of using tri-O-acetyl derivative of shikimic acids. The details of synthetic procedures for cationic amphiphiles Y with quinic acid head-groups are described below in Example 2 for synthesis of cationic amphiphile 2 (as a representative example). Synthetic routes followed in preparing the mannosyl analog (3) of the presently described cationic amphiphiles are shown schematically in Scheme 3 and the synthetic details for the preparation of the cationic amphiphile 3 are provided below in Example 3. Structures of all the synthetic intermediates and target cationic amphiphiles shown in Schemes 1-3 were confirmed by $^1$H NMR and ESI mass spectroscopy and the purities of all the target cationic amphiphiles were confirmed by reverse phase analytical HPLC using two different mobile phases.

Scheme 1: Synthesis of Lipid (X) with mannose mimicking Shikmic Acid Head Group:

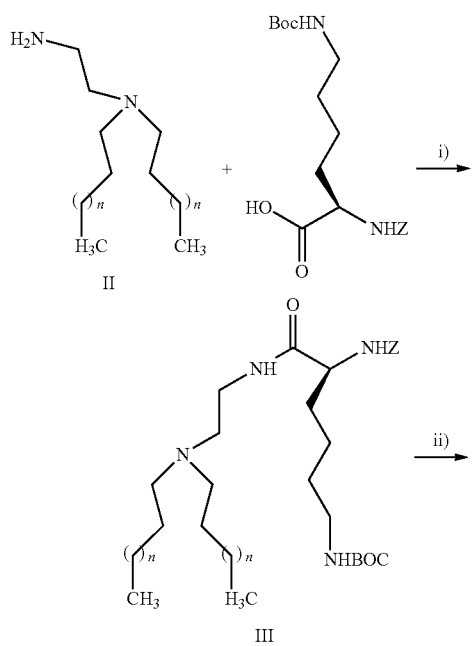

13
-continued
14
-continued
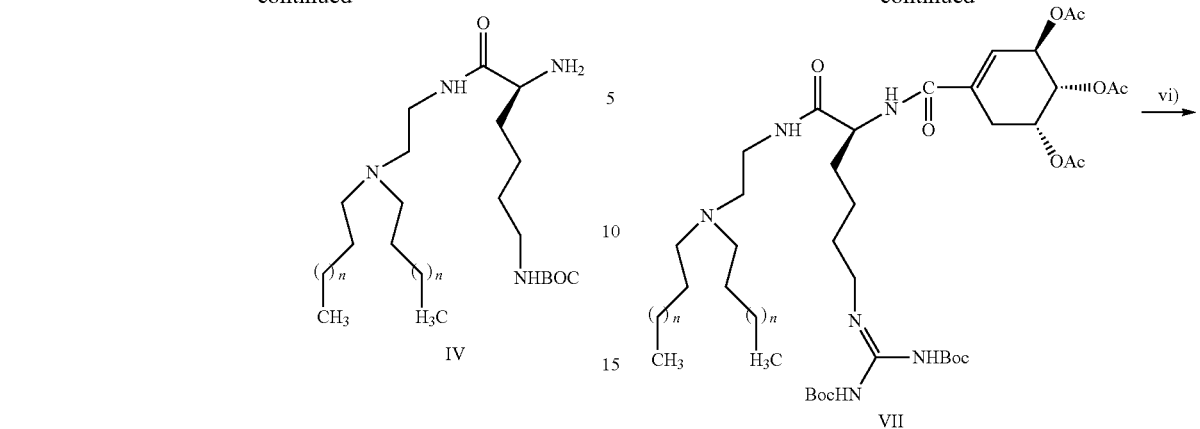
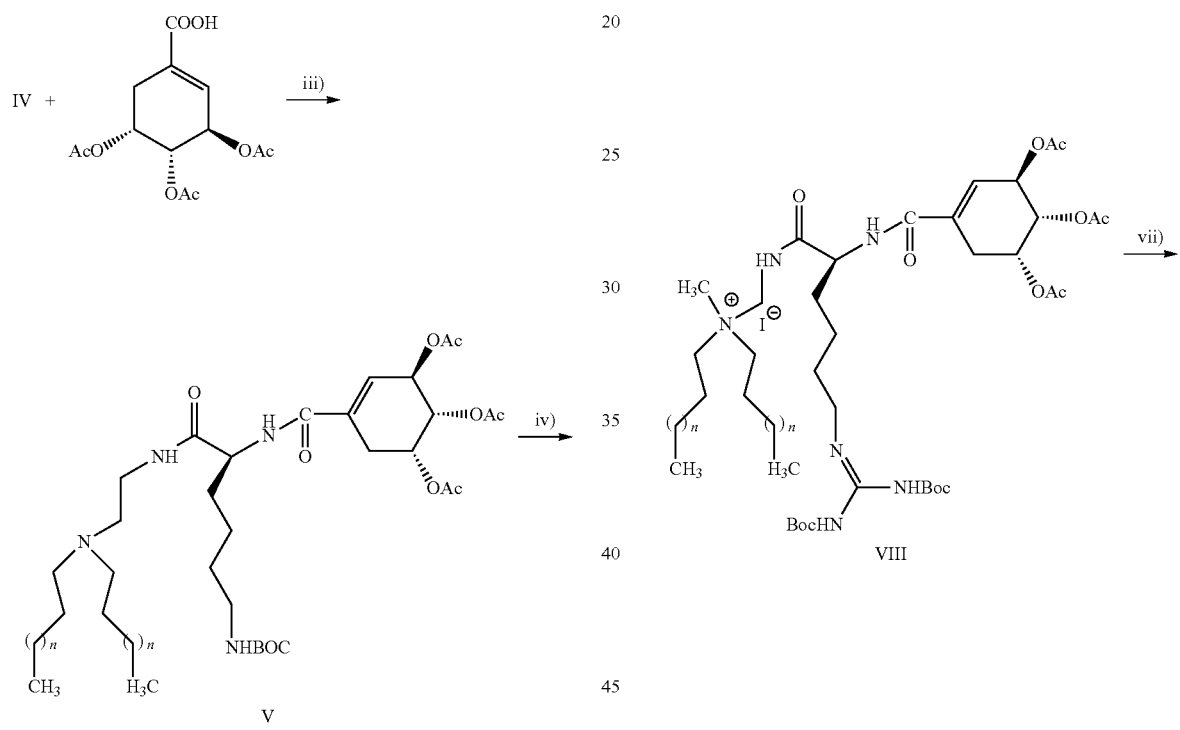
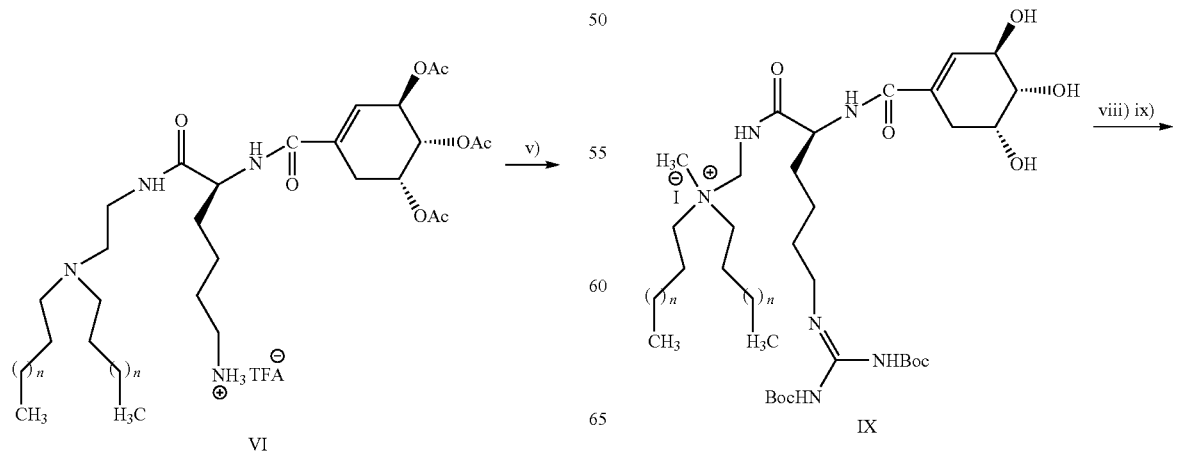

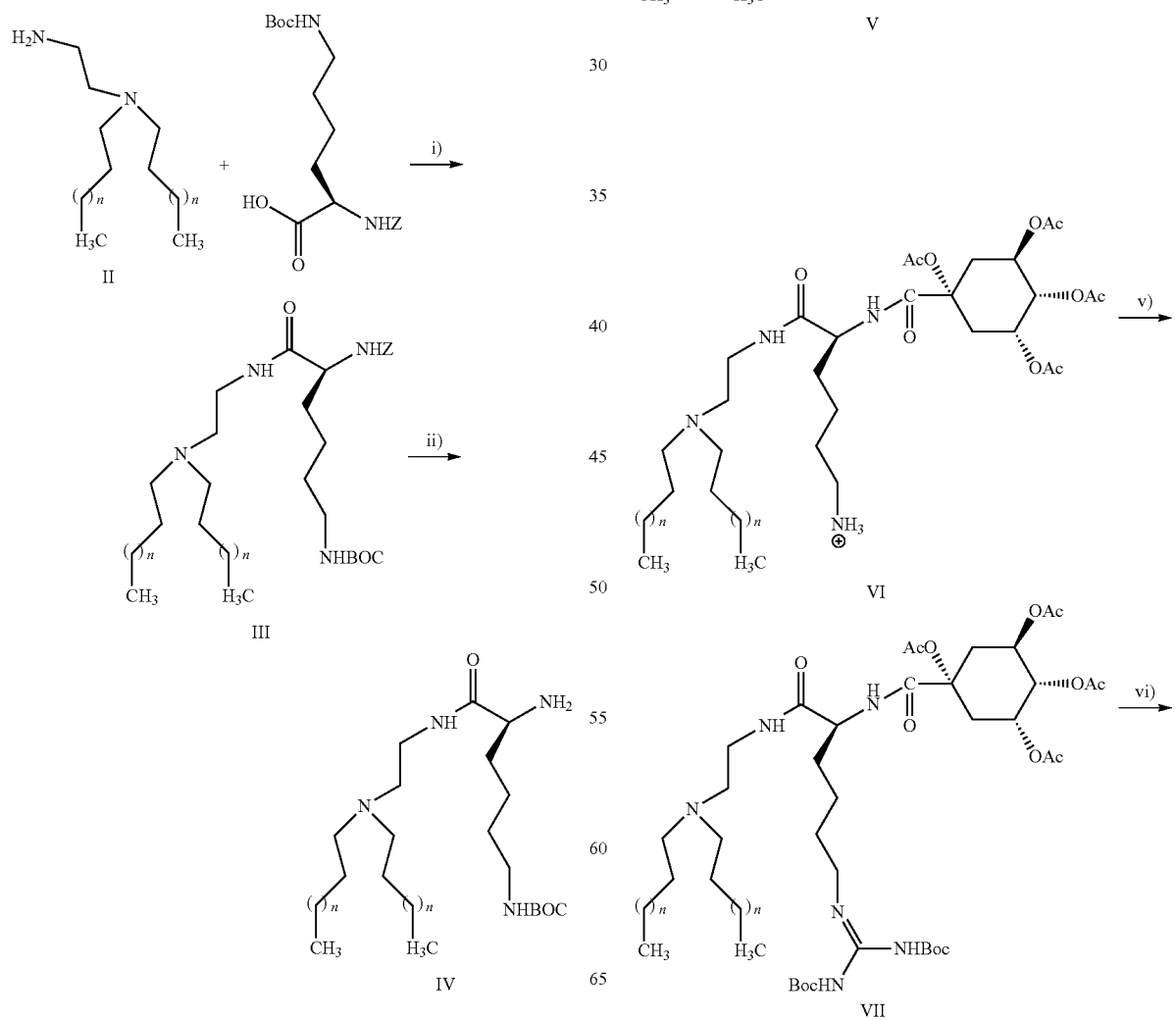
Reagents: i) EDCl, HOBt, DIPEA and DCM; ii) Pd(OH)$_2$—C, MeOH, EtOAc, H$_2$; iii) EDCI, HOBt, DIPEA and DCM; iv) TFA, DCM, 0° C.; v) Di-Boc-thiourea, Et$_3$N, HgCl$_2$; vi) CH$_3$I, DCM; vii) MeOH, K$_2$CO$_3$, Amberlite IRP64 for H$^+$ ion exchange; viii) TFA, DCM, 0° C.; ix) Amberlyst A-26 resin for Cl$^-$ ion exhange;
Scheme 2: Synthesis of Lipid (Y) with mannose mimicking Quinic Acid Head Group:

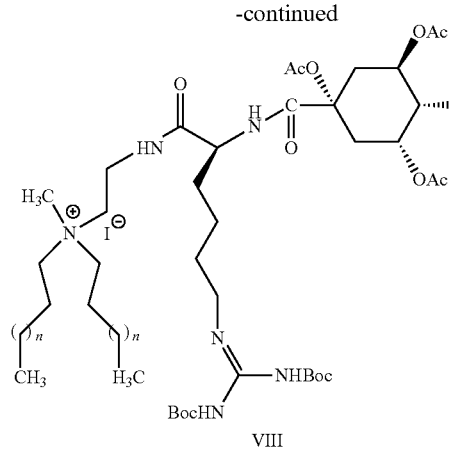
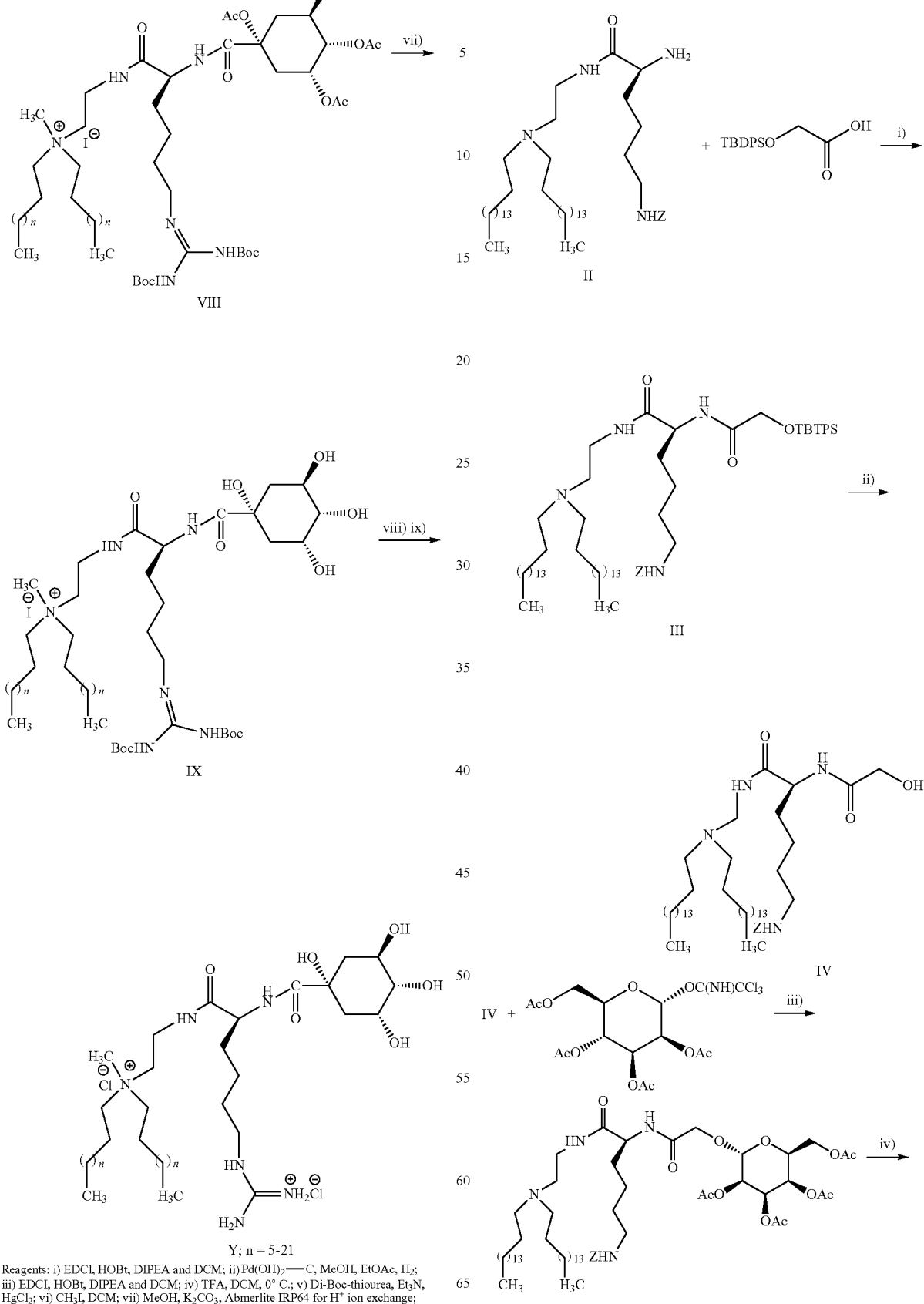
Scheme 3: Synthesis of Lipid 3 with control mannosylated Head Group:
Reagents: i) EDCl, HOBt, DIPEA and DCM; ii) Pd(OH)$_2$—C, MeOH, EtOAc, H$_2$; iii) EDCl, HOBt, DIPEA and DCM; iv) TFA, DCM, 0° C.; v) Di-Boc-thiourea, Et$_3$N, HgCl$_2$; vi) CH$_3$I, DCM; vii) MeOH, K$_2$CO$_3$, Abmerlite IRP64 for H$^+$ ion exchange; viii) TFA, DCM, 0° C.; ix) Amberlyst A-26 resin for Cl$^-$ ion exhange;

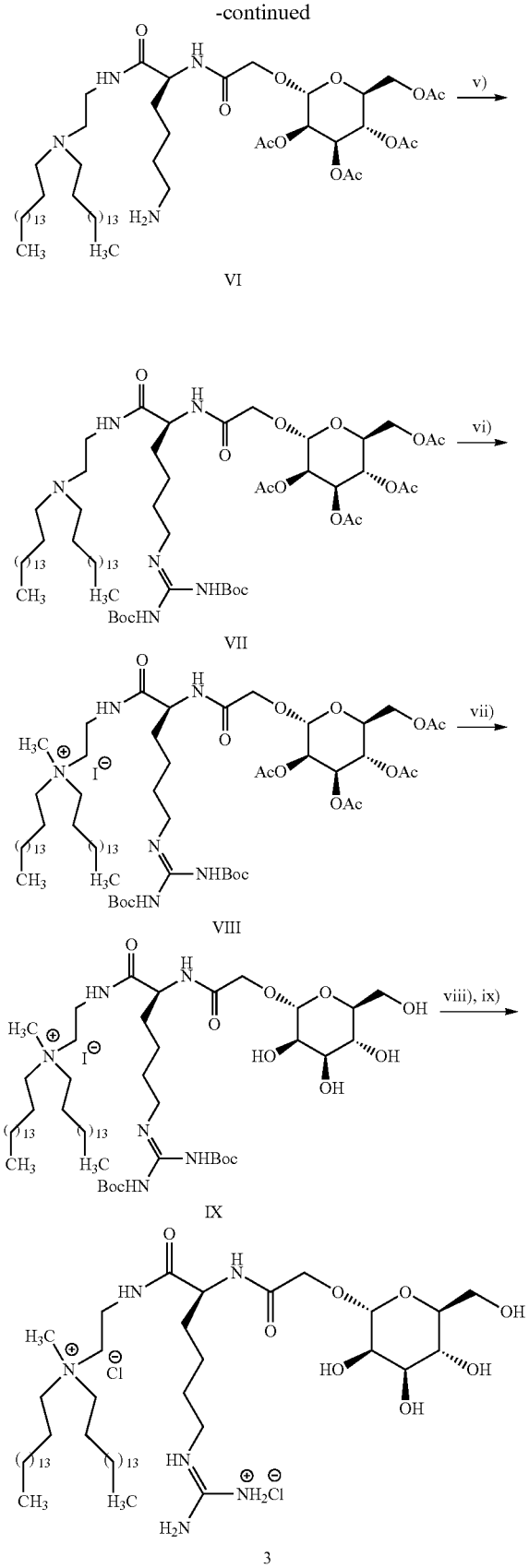

Reagents: i) EDCl, HOBt, DIPEA and DCM; ii) TBAF, THF; iii) BF₃OEt₂, DCM, -15° C., 3 hrs; iv) Pd(OH)₂—C, MeOH, EtOAc, H₂; v) Di-Boc-thiourea, Et₃N, HgCl₂; vi) CH₃I, DCM; vii) MeOH, K₂CO₃, Abmerlite IRP64 for H⁺ ion exchange; viii) TFA:DCM, (1:2), 0° C.; ix) Amberlyst A-26 resin for Cl⁻ ion exhange;

Formulations

The present invention also provides novel formulation comprising optimal amounts of cationic amphiphiles compound of formula I, with mannose-mimicking head-groups disclosed herein, biological macromolecules and the co-lipids. One or more additional physiologically acceptable substances may be included in the pharmaceutical formulation of the invention to stabilize the formulation for storage or to facilitate successful intracellular delivery of the biologically active molecules. Co-lipids according to the practice of the present invention are useful in mixing with one or more of the glycomimicking amphiphiles. Cholesterol is an excellent co-lipid for use in combination with the presently described amphiphiles to facilitate successful delivery of the biologically active molecules in general and DNA vaccines in particular to APCs. A preferred range of molar ratio of the cationic amphiphile to co-lipid is 1:1. As such, it is within the art to vary the said range to a considerably wide extent. Typically, liposomes were prepared by dissolving the cationic amphiphiles and the co-lipid (Cholesterol or DOPE) in the appropriate mole ratio in a mixture of methanol and chloroform in a glass vial. The solvent was removed with a thin flow of moisture free nitrogen gas and the dried lipid film was then kept under high vacuum for 8 h. The dried lipid film was hydrated in sterile deionized water in a total volume of 1 mL at cationic lipid concentration of 1 mM for a minimum of 12 h. Liposomes were vortexed for 1-2 minutes to remove any adhering lipid film and sonicated in a bath sonicator (ULTRAsonik 28X) for 2-3 minutes at room temperature to produce multilamellar vesicles (MLV). MLVs were then sonicated with a Ti-probe (using a Branson 450 sonifier at 100% duty cycle and 25 W output power) for 1-2 minutes to produce small unilamellar vesicles (SUVs) as indicated by the formation of a clear translucent solution. Biologically active molecules that can be administered intracellularly in therapeutic amounts using the cationic amphiphiles of the present invention include ribosomal RNA, antisense polynucleotide of RNA or DNA, polynucleotide of genomic DNA, cDNA or mRNA that encodes for a therapeutically important antigen or protein. The cationic amphiphiles with mannose-mimicking head-groups disclosed herein may be blended such that one or more of the representatives thereof may be used in a combination to facilitate entry of the said biologically active molecules into cells/tissues.

In a further embodiment, the cationic amphiphiles disclosed in the present invention may be used either in pure form or in combination with other lipids or helper lipids such as cholesterol, phosphatidylethanolamine, phosphatidylglycerol, etc. The said therapeutic formulation may be stored at 0-4° C. until complexed with the biologically active therapeutic molecules. Agents that prevent bacterial growth and increase the shelf life may be included along with reagents that stabilize the preparation, e.g., low concentrations of glycerol. It is specifically warned that freezing and thawing cycles could cause loss in efficiency of the formulation.

In yet another embodiment, the formulation of the cationic amphiphiles disclosed herein, co-lipids (cholesterol or DOPE) and the biologically active therapeutic molecules may be administered intravenously besides other routes such as subcutaneous, intramuscular and intraperitonial. Further, the said formulations may be administered to cells at a ratio of 0.1-0.5 microgram of DNA to 50,000 cells in an in vitro system. The amount of cationic amphiphiles could be varied within the cationic amphiphile to DNA charge ratio of 0.3:1 to 9:1 considering two positive charges for one cationic amphiphile and one negative charge of a single nucleotide base.

The invention further provides a process for the preparation of the said formulation comprising the steps of preparing a dispersion of the cationic amphiphiles disclosed in the present invention; contacting said dispersion with a biologically active molecule to form a complex between the said cationic amphiphiles and the said biologically active molecules and contacting the cells with the said complex thereby facilitating transfer of said biologically active molecules into the cells. The present invention also provides with various formulations that facilitate intracellular delivery of biologically active molecules.

Figure 4:
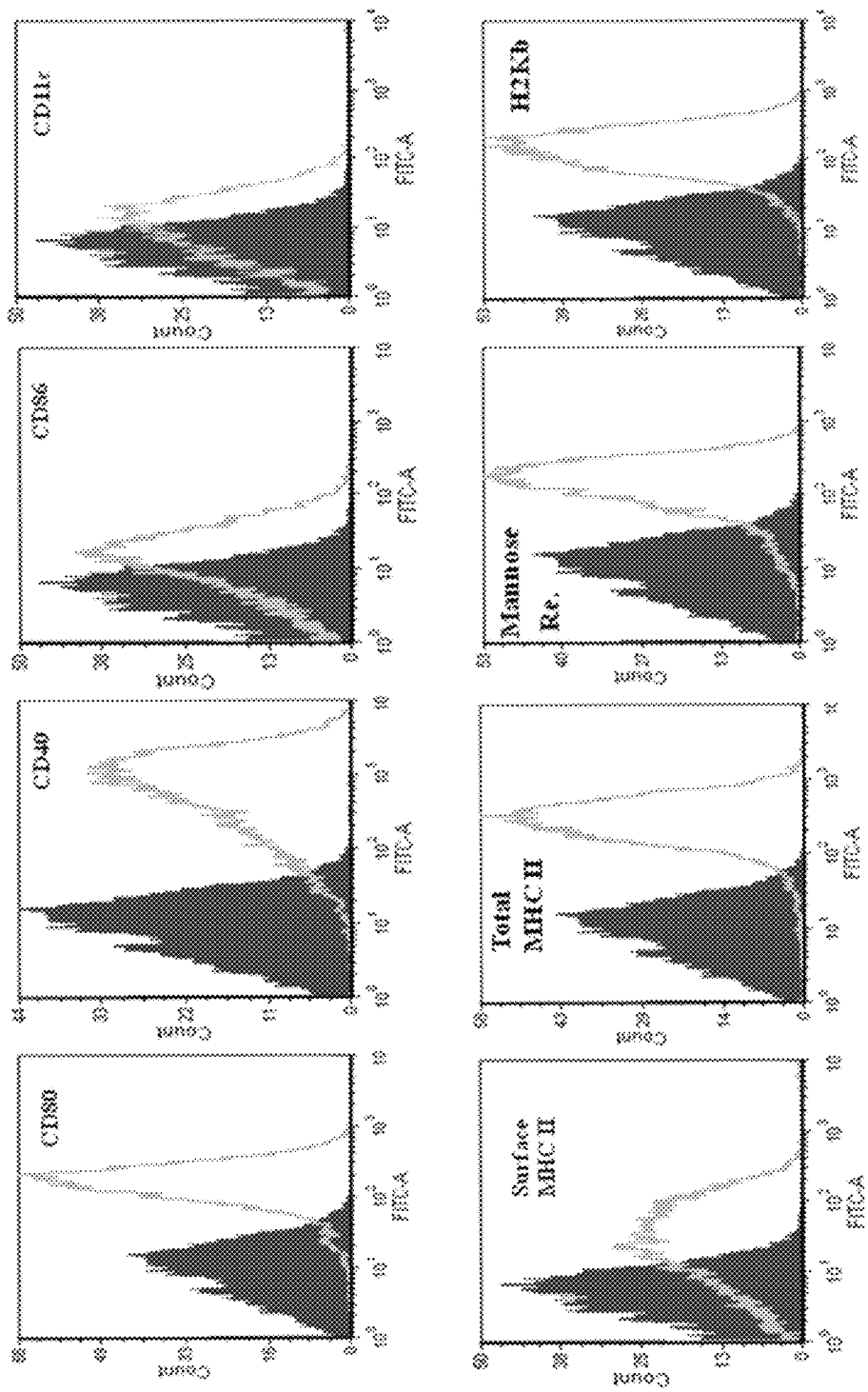
FIG. 4 confirms the presence of DCs surface markers including cell surface MHC II, total MHC II, mannose-receptors, CD11c, CD80, $H_2Kb$, CD86 and CD40 in isolated mbmDCs by flow cytometry. ~$5 \times 10^5$ mbmDCs were stained with non-conjugated monoclonal antibodies specific for the cell surface MHC II, total MHC II (total of surface & intracellular MHC II), Phycoerythrin (PE) conjugated monoclonal antibodies for mannose receptor, and FITC conjugated monoclonal antibodies for CD11c, CD80, $H_2kb$, CD86 and CD40. For measuring MHC-II marker profile, mbmDCs were stained with FITC-conjugated secondary antibody after staining with anti-MHC-II monoclonal antibody. Each experiment was repeated three times and similar markers profiles were observed in each time.

Transfection of Dendritic Cells (DCs) Via Mannose Receptors:

Among the various APCs, DCs are the most potent antigen presenting cells, capable of effective antigen presentation to naïve T cells (Romini N, et al. J Exp Med. 1994; 180:83-93). In the field of DNA vaccination, transfected DCs are the key players for efficient cytotoxic T-lymphocyte (CTL) responses (Denis-Mize K S, et al. Gene Ther. 2000; 24:2105-112, Condon C, et al. Nat Med. 1996; 10: 1122-1128, Akbari O, et al. J Exp Med. 1999; 189:169-178, Coombes B. K. et al. Immunol Lett. 2001; 78:103-111, Porgador A, et al. J Exp Med. 1998; 188:1075-1082, Timares L, et al. J Immunol. 2003; 170:5483-5490, Sbai H, et al. Vaccine. 2002; 20:3137-3147, Irvine A S, et al. Nat Biotechnol. 2000; 18:1273-1278). For a successful DNA vaccination and antigen presentation by DCs, DNA internalization or DNA loaded DCs are not sufficient. The antigen encoded DNA vaccine needs to be delivered to the nucleus of the dendritic cell in order to express the respective antigen. Then the antigens are processed and displayed on MHC class I and class II molecules of activated DCs (Samantha J, et al. Advanced Drug Delivery Reviews 2005; 57:377-390). Effective transfection to DCs is restricted by the lysosomal or phagosomal degradation of the internalized DNA before its transportation to nucleus. This is why DCs are hard-to-transfect. The transfection rates differ greatly from one group to other with the transfection efficiencies ranging from 0-10% (Alijagic S, et al. Eur J Immunol. 1995; 25:3100-3107, Arthur J. F. et al. Cancer Gene Ther. 1997; 1:17-25, Lohmann S, et al. Cancer Gene Ther. 2000; 4:605-14, Strobel I, et al. Gene Ther. 2000; 23:2028-35). The mannose receptor (MR) expressed on the surface of immature DCs are involved in endocytosis and phagocytosis (Ezekowitz, R A B, et al. J. Exp. Med. 1990; 172:1785-1794). First, the transfection efficiency of the cationic amphiphiles 1, 2 & 3 were evaluated in mouse bone marrow derived dendritic cells. To this end, the immature dendritic cells were isolated from the bone marrow of C57BL/6J mice by culturing with GM-CSF and IL-4 following a previously described protocol (Inaba K, et al. J Exp Med 1992; 176: 1693-1702). First, the presence of various DC markers in the isolated mbmDCs were confirmed by fluorocytometric analysis. The freshly isolated mbm DCs were treated with FITC/PE conjugated monoclonal antibodies for various DC markers and their FACS profiles monitored. Findings in flow cytometry confirmed the characteristics of immature DCs having high intracellular levels of MHC class II molecules, low CD 86, high levels of CD11c, CD 40 and mannose receptor (FIG. 4).

Figure 2:
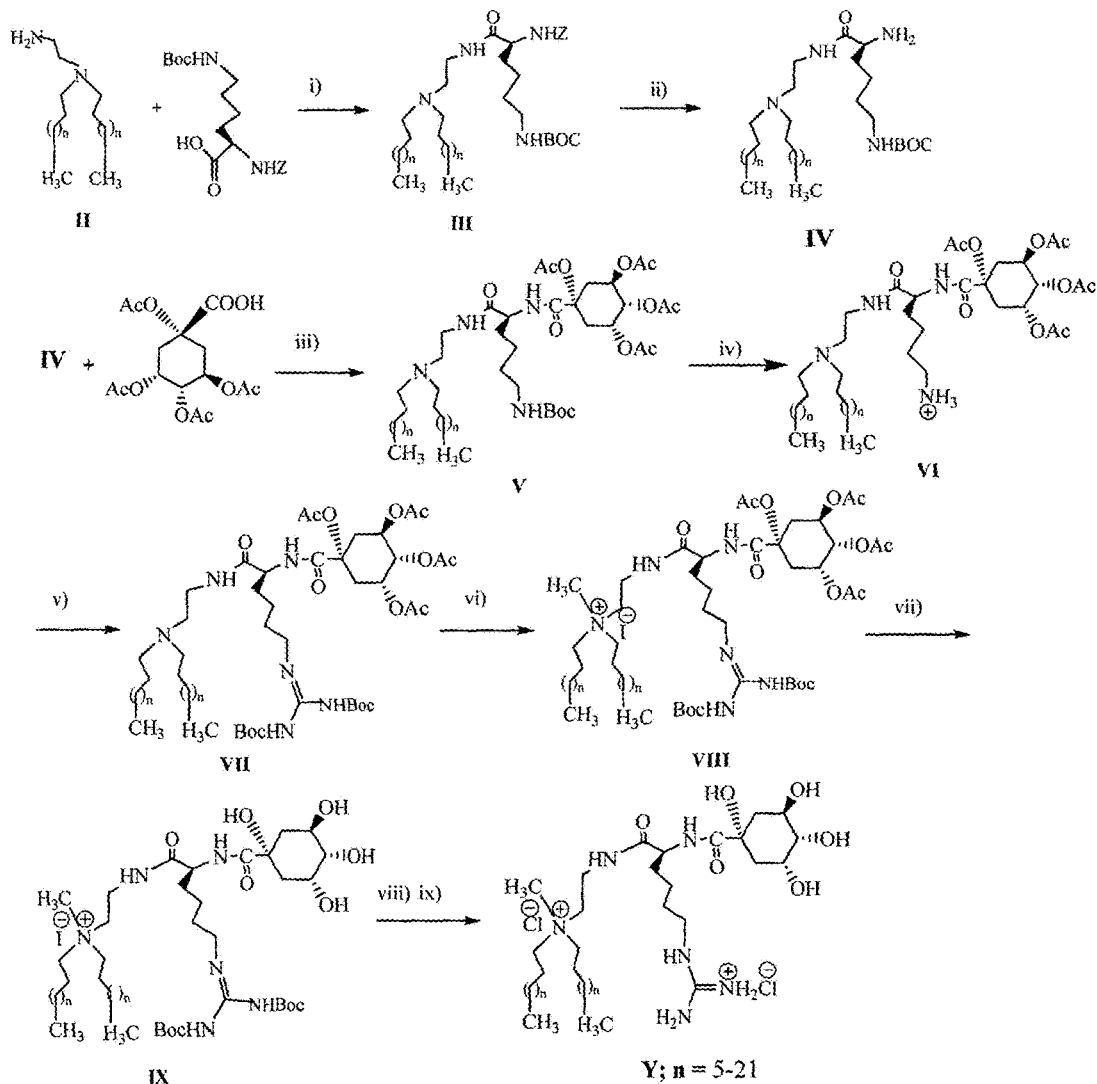
FIG. 2 (Scheme 2) is a schematic representation of the synthetic procedures used for the preparation of cationic amphiphiles containing mannose-mimicking quinoyl head-groups.
Figure 3:
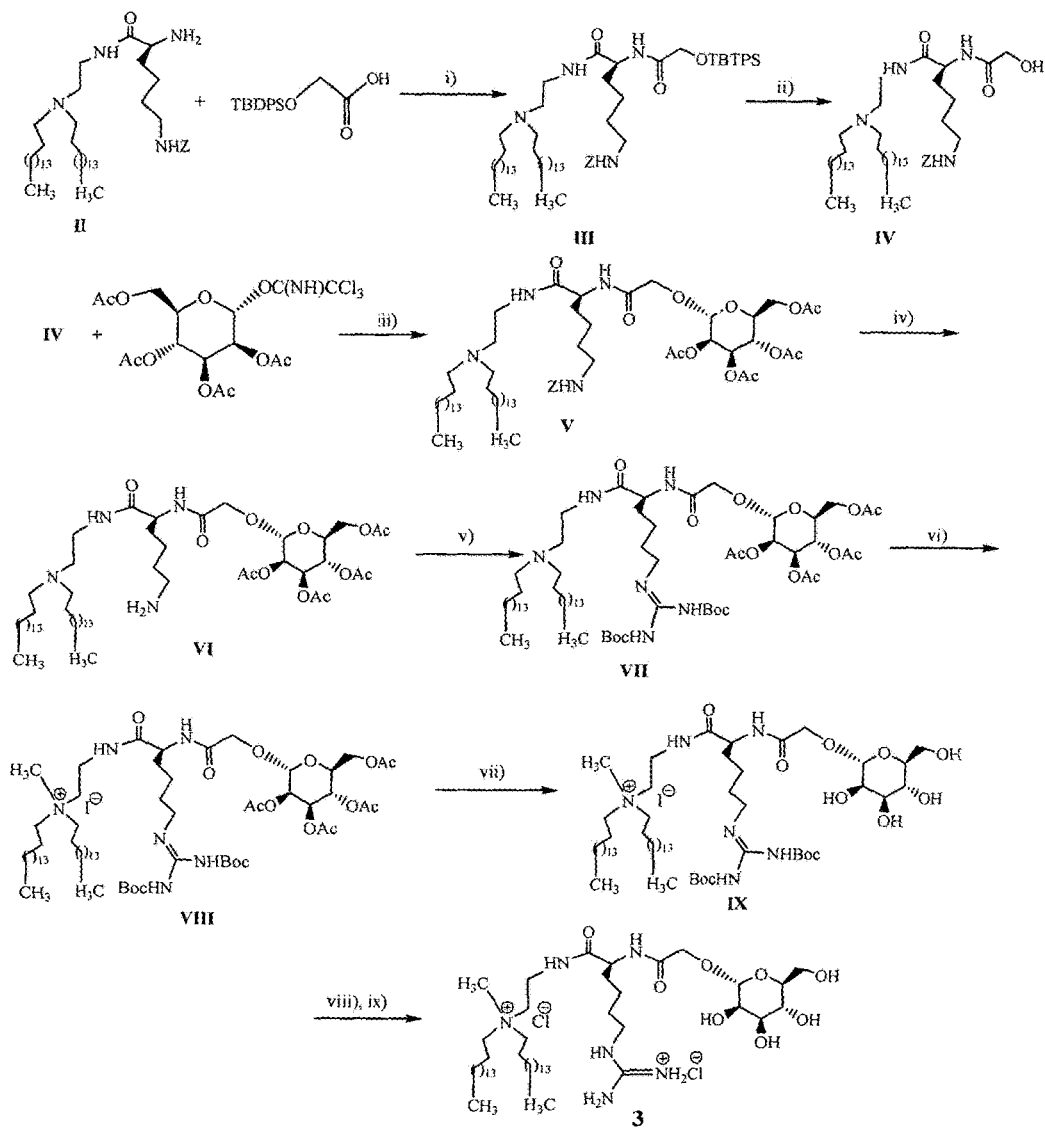
FIG. 3 (Scheme 3) is a schematic representation of the synthetic procedures used for the preparation of cationic amphiphile 3 containing a mannosyl head-group.
Figure 6:
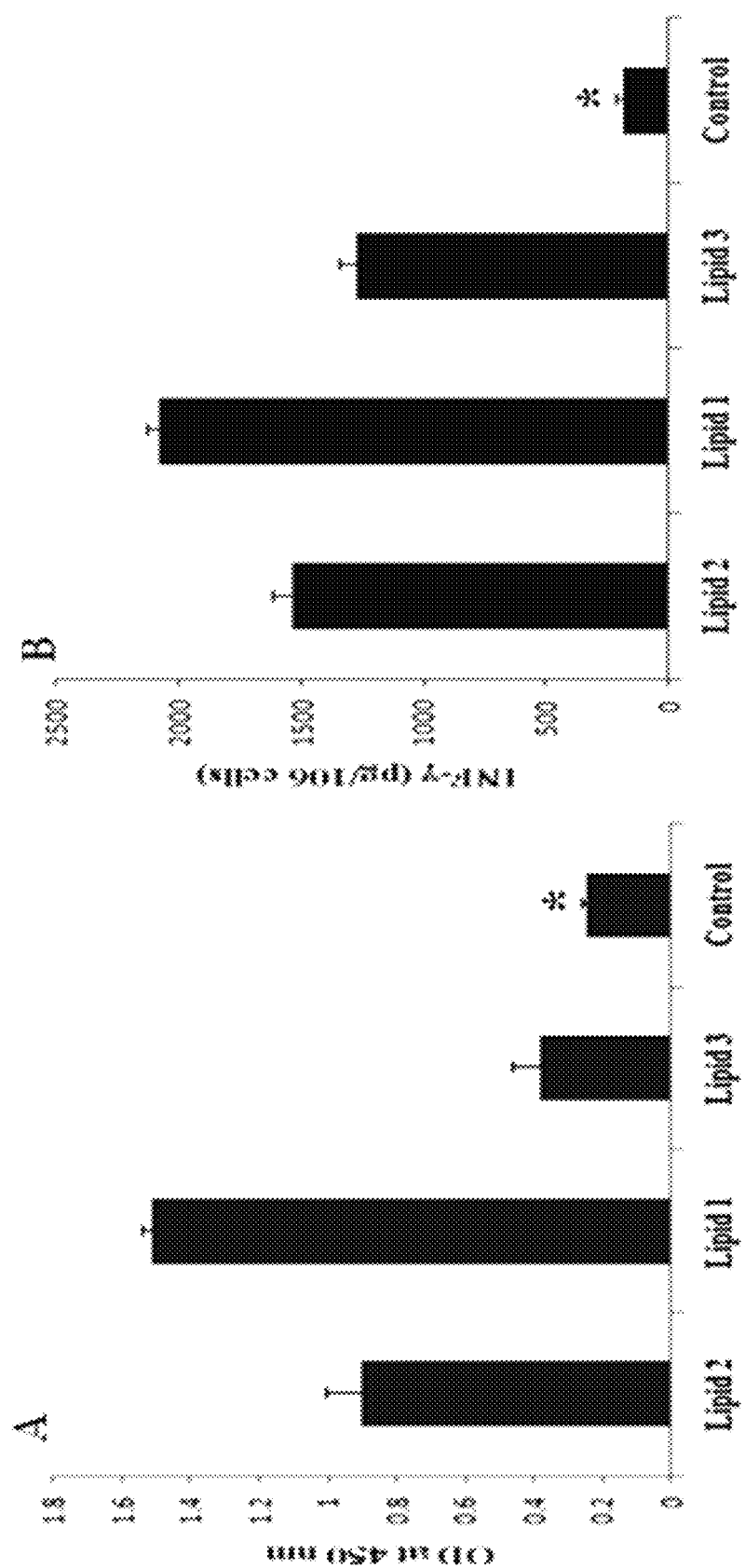
FIG. 6 summarizes humoral and cellular immune responses in C57BL/6J mice upon subcutaneous administration of lipoplexes of 1, 2 & 3 and p-CMV-β-gal as a model genetic vaccine. A) 6-8 weeks old female C57BL/6 mice (each weighing 20-22 g, n=4) were immunized subcutaneously with lipoplexes of 1, 2 & 3 and p-CMV-β-gal as a model genetic vaccine (150 μl in 5% glucose solution, 15 μg DNA, 4:1 lipid:DNA ratio three times with a seven-day interval). Two weeks after the third immunization, serum samples were collected from mice and assayed for β-gal antibodies by ELISA. The Y-axis represents absorbance obtained with a 1:200 dilution of serum (*$P<0.005$ for cationic amphiphiles 1, 2 & 3 compared with values for untreated mice). B) Two weeks after the second immunization, splenocytes were collected and used immediately (without in vitro restimulation) for T-cell (cellular) responses by ELISA (*$P<0.005$ for the cationic amphiphiles 1, 2 & 3 compared with values for untreated mice).
Figure 7:
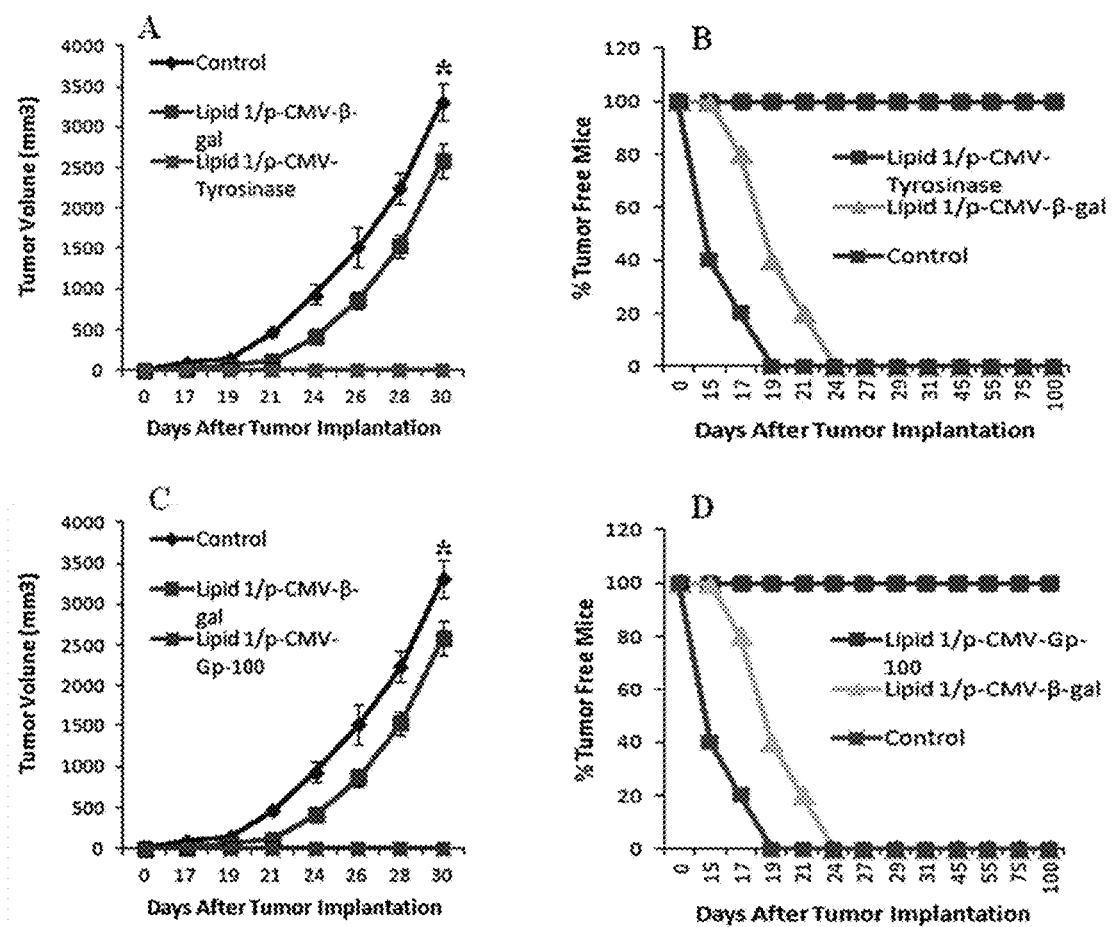
FIG. 7 depicts long-lasting tumor protection in syngeneic mice immunized with lipoplex of p-CMV-tyrosinase & p-CMV-gp100 and lipid 1. A, C) 6-8 weeks old female syngeneic C57BL/6 mice (each weighing 20-22 g, n=6) were immunized (s.c) with: lipoplexes of lipid 1 & p-CMV-Tyrosinase (A); lipoplexes of lipid 1 & p-CMV-gp100 (C); lipoplexes of lipid 1 & p-CMV-β-gal (using 150 μL 5% glucose solution containing 15 μg DNA, 4:1 lipid:DNA ratio, three times with a seven-day interval). Two weeks post third immunization; mice were challenged with lethal melanoma tumor by subcutaneous injection of ~$1 \times 10^5$ B16F10 cells. Tumor volumes (V=½ $ab^2$ where, a=maximum length of the tumor and b=minimum length of the tumor measured perpendicular to each other) were measured with a slide calipers for up to 29 days. Results represent the means+/−SD for n=5 tumors (*$P<0.005$ vs. tumor sizes for lipoplexes of lipid 1 & p-CMV-β-gal). B, D) The percentage of tumor-free mice immunized (s.c.) with: lipoplexes of lipid 1 & p-CMV-Tyrosinase (B); lipoplexes of lipid 1 & p-CMV-Gp-100 (D); lipoplexes of lipid 1 & p-CMV-β-gal and subsequently challenged with melanoma tumor as described above.

After confirming the presence or expected DC markers on the surface of the isolated DCs (FIG. 4), mbmDCs were transfected with a GFP plasmid in complexation with the liposomes of 1-3 (prepared in combination with equimolar 1,2-di-oleyol-sn-glycero-3-phosphoethanolamine, DOPE, as co-lipid) both in presence and in absence of mannan, a natural ligand of mannose receptor and evaluated transfection efficiencies by flow cytometry. Lipoplexes of 1 & 2 were about 4 & 2.5 times more efficient than the lipoplex of the control mannosyl analog 3 (~20% for lipoplex of 1, 10-12% for lipoplex of 2 and vs 4-5% for lipoplex of 3) in transfecting mbmDCs (FIG. 2, upper panel). mbmDCs are hard to transfect. LipofectAmine2000, a widely used commercially available liposomal transfection kit, was essentially incompetent in transfecting mbmDCs (FIG. 2). The efficiencies of all the three lipids 1-3 in transfecting mbm-DCs were adversely affected when mbmDCs were pre-incubated with mannan, a natural ligand for mannose receptor (FIG. 2, lower panel). Taken together, the transfection profiles of lipids 1-3 (FIG. 2) are consistent with mbmDC transfection by the lipoplexes of lipids 1-3 being mediated by the mannose receptors expressed on the cell surfaces of the dendritic cells Humoral Immune Response Upon Subcutaneous Genetic Immunization in Mice:

The therapeutic potential of the presently described glycomimicking cationic amphiphiles as DNA vaccine carriers were evaluated by subcutaneously immunizing C57BL/6J mice (three times with seven days interval) with lipoplexes of lipids 1-3 in complexation with 15 μg of pCMV-SPORT-β-gal (as a model antigen encoded DNA) at lipid:DNA charge ratio of 4:1. Two weeks after subcutaneously immunizing C57BL/6J mice with mbmDCs pre-transfected with lipoplexes of pCMV-SPORT-β-gal & lipids 1-3, splenocytes and sera were collected for measuring both INF-γ and anti-β-gal antibody (signature cytokines for cellular and humoral immune responses, respectively). Untreated mice were used as control. The amount of INF-γ from splenocytes and the amount of β-gal antibodies from sera of immunized mice were found to be significantly higher than those for mice immunized with untreated mice. (FIG. 6)

Long-lasting tumor protection in syngeneic mice upon subcutaneous genetic immunization in mice:

Toward evaluating immune response after direct subcutaneous administration of the presently described lipoplexes of DNA vaccines p-CMV-Gp-100 & p-CMV-Tyrosinase encoding melanoma antigens gp100 and tyrosinase, C57BL/6J syngeneic mice were immunized with the lipoplexes of lipids 1 (150 μl in 5% glucose solution, 15 μg DNA, 4:1 lipid:DNA ratio three times with a seven-day interval). The immunized mice (n=5) were subsequently challenged with lethal dose of melanoma tumor (~1×10$^5$ B16F10 cells). Tumor growth was monitored for 29 days since the control mice group immunized with lipid 1 had to be sacrificed at that point of study (tumor sizes became quite large, FIG. 4A, C). All the mice immunized with lipoplexes of lipids 1 & p-CMV-Gp-100 and lipid 1 & p-CMV-Tyrosinase lived a tumor free life post tumor challenge during the 29 days tumor growth inhibition studies (FIG. 4A, C). Importantly, remarkably long-lasting (100 days post tumor challenge) anti-melanoma protective immunity was observed in all the mice (n=5) immunized with lipoplexes of lipids 1 & p-CMV-Gp-100 and lipid 1 & p-CMV-Tyrosinase during 100 days post tumor challenge (FIG. 4B, D). Thus, the findings summarized in FIG. 4A-D convincingly demonstrated enhanced systemic potential of cationic amphiphiles with mannose-mimicking shikimoyl ead-groups in genetic immunization under in vivo settings. Importantly, all mice died within 30 days when mice were immunized with lipoplex of lipid 1 and p-CMV-β-gal, a control irrelevant plasmid encoding the enzyme β-galactosidase (FIG. 4A, C).

These findings demonstrated that the presently observed remarkably sustained protective immune response in genetic immunization is antigen-specific.

The following examples are given by way of illustration of the present invention and therefore should not be construed to limit the scope of the present invention.

Example 1

Synthesis of the Cationic Amphiphile 1 (Scheme 1, X, n=13).

Step (i): Solid HOBt (0.28 g, 2 mmol) and EDCI (0.4 g, 2 mmol) were added sequentially to an ice cold and stirred solution of $N^{\alpha}$—Z—$N^{\epsilon}$—BOC-L-Lysine (0.76 g, 2 mmol) in 5 mL dry DCM/dry DMF (9:1, v/v) under nitrogen atmosphere. After half an hour, N-2 aminoethyl-N,N-di-n-hexadecylamine (0.8 g, 1.5 mmol) dissolved in dry DCM was added to the reaction mixture. The resulting solution was left stirred at room temperature overnight, diluted with excess DCM and washed sequentially with saturated sodium bicarbonate (~2×50 mL) and water (~2×50 mL). The organic layer was dried over anhydrous sodium sulfate, filtered and the solvent from the filtrate removed by rotary evaporation. The residue upon column chromatographic purification with 60-120 mesh silica gel using 1-1.5% methanol in dichloromethane (v/v) as eluent afforded 1.1 g (80% yield) of the pure intermediate III. ($R_f$=0.5, 5% methanol in dichloromethane, v/v).

$^1$H NMR (300 MHz, CDCl$_3$): δ/ppm=0.9 [t, 6H, C$\underline{H}_3$—(CH$_2$)$_{13}$—]; 1.2-1.9 [m, 54H, —C$\underline{H}_2$(CH$_2$)$_{13}$—; 9H, CO—O—C(C$\underline{H}_3$)$_3$; 6H, LysC$^\gamma\underline{H}_2$, LysC$^\delta\underline{H}_2$, LysC$^\beta\underline{H}_2$]; 2.4-2.7 [m, 4H, —N(—C$\underline{H}_2$—CH$_2$—)$_2$; 2H, —N—C$\underline{H}_2$—CH$_2$—NH—CO] 3.0-3.1 [m, 2H, LysC$^\omega\underline{H}_2$]; 3.3-3.4 [m, 2H, —N—CH$_2$—C$\underline{H}_2$—NH—CO]; 4.0 [m, 1H, BOC—N$\underline{H}$]; 4.5 [m, 1H, LysC$^\alpha\underline{H}$]; 5.0 [d, 2H, —O—C$\underline{H}_2$—C$_6$H$_5$]; 5.5 [m, 1H, —N$\underline{H}$—Z]; 7.2-7.5 [m, 5H, O—CH$_2$—C$_6\underline{H}_5$].

Step (ii): The intermediate III prepared in above step (1.1 g, 1.2 mmol) was dissolved in 8 mL methanol and 2 drop of 2N hydrochloric acid. Pd(OH)$_2$/C (0.3 g) was added to the reaction mixture and air was removed. The resultant reaction mixture was stirred at room temperature for 14 h under hydrogen atmosphere (2 atmos). The reaction mixture was filtered using celite and the filtrate was dried over anhydrous sodium sulphate and the solvent from the filtrate removed by rotary evaporation afforded the 0.9 g (90% yield) of pure intermediate IV. ($R_f$=~0.4, 10% methanol-chloroform, v/v).

Step (iii) Solid HOBt (0.1 g, 1.4 mmol) and EDCI (0.15 g, 1.4 mmol) were added sequentially to an ice cold and stirred solution of 3,4,5-Triacetoxycyclohex-1-ene carboxylic acid (0.23 g, 1.4 mmol) in 5 mL dry DCM/dry DMF (9:1, v/v). After half an hour, the intermediate IV prepared in above step (0.4 g, 0.54 mmol) was dissolved in 4 mL dry DCM (neutralized with 0.4 mL of tri ethylene amine) was added to the reaction mixture. The resulting solution was left stirred at room temperature overnight, diluted with excess DCM and washed sequentially with saturated sodium bicarbonate (~2×40 mL) and water (~2×40 mL). The organic layer was dried over anhydrous sodium sulfate, filtered and the solvent from the filtrate removed by rotary evaporation. The residue upon column chromatographic purification with 60-120 mesh silica gel using 1.5-2% methanol in dichloromethane (v/v) as eluent afforded 0.4 g (72% yield) of the pure intermediate V. ($R_f$=0.5, 5% methanol in dichloromethane, v/v).

$^1$H NMR (300 MHz, CDCl$_3$): δ/ppm=0.9 [t, 6H, C$\underline{H}_3$—(CH$_2$)$_{13}$—]; 1.2-1.5 [m, 54H, 2×—C$\underline{H}_2$(CH$_2$)$_{13}$—; 9H,CO—O—C(C$\underline{H}_3$)$_3$]; 1.6-1.9 [m, 6H, LysC$^\gamma\underline{H}_2$, LysC$^\delta\underline{H}_2$, LysC$^\beta\underline{H}_2$]; 2.0-2.1 [3s, 9H, 3×—COC$\underline{H}_3$]; 2.2-2.4 [dd, 2H, shik6-H,H']; 2.7-3.2 [m, 4H, —N(—C$\underline{H}$—CH$_2$—)$_2$; 2H, —N—C$\underline{H}_2$—CH$_2$—NH—CO; 2H, LysC$\overline{H}^\omega\underline{H}_2$]; 3.4-3.5 [m, 2H, —N—CH$_2$—C$\underline{H}_2$—NH—CO]; 4.3-4.4 [m, 1H, LysC$^\alpha\underline{H}$]; 4.7 [m, 1H, BOC—N$\underline{H}$]; 5.1-5.3 [m, 2H, shik-4-H, shik-5-H]; 5.6-5.7 [m, 1H, shik-3-H]; 6.4 [d, 1H, shik-2-H]; 7.1 [m, 1H, CO—N$\underline{H}$].

ES-MS: m/z=1020 [M+1]$^+$ for C$_{58}$H$_{106}$N$_4$O$_{10}$.

Step (IV): The intermediate V (0.5 g, 0.5 mmol) prepared in above step was dissolved in dry DCM (4 mL) and TFA (2 mL) was added at 0° C. The resulting solution was left stirred at 0° C. for 3 h to ensure complete deprotection. Excess TFA was removed by nitrogen flushing. The resulting compound was dissolved in chloroform (80 mL) and washed with aqueous saturated NaHCO$_3$ (3×90 mL), brine (1×70 mL). The organic layer was dried over anhydrous sodium sulfate, filtered and the solvent from the filtrate removed by rotary evaporation afforded 0.41 g (91% yield) of free amine as intermediate VI.

Step (V): Mercury chloride (0.28 g, 1.0 mmol) was added to a mixture of intermediate VI (prepared in step IV, 0.4 g. 0.4 mmol), bis-N-Boc-thiourea (0.2 g, 0.7 mmol) dissolved in dry N,N-dimethylformamide (DMF, 2 mL), Triethylamine (1 mL) and dry dichloromethane (DCM, 5 mL) at 0° C. with continuous stirring. The resulting mixture was stirred at 0° C. under nitrogen for 40 min, diluted with ethyl acetate (20 mL), and filtered through a pad of Celite. The filtrate was sequentially washed with water (2×50 mL) and brine solution (2×50 mL), dried over anhydrous sodium sulfate, and filtered, and the solvent from the filtrate was removed by rotary evaporation. The residue upon column chromatographic purification with 60-120 mesh silica gel using 2-2.5% methanol/dichloromethane (v/v) as eluent afforded 0.41 g of the pure intermediate VII (71%, Rf-0.5, 5% methanol/dichloromethane, v/v).

$^1$H NMR (300 MHz, CDCl$_3$): δ/ppm=0.9 [t, 6H, C$\underline{H}_3$—(CH$_2$)$_{13}$—]; 1.2-1.5 [m, 54H, 2×—C$\underline{H}_2$(C$\underline{H}_2$)$_{13}$—; 18H,CO—O—C(C$\underline{H}_3$)$_3$]; 1.6-1.9 [m, 6H, LysC$^\gamma\underline{H}_2$, LysC$^\delta\underline{H}_2$, LysC$^\beta\underline{H}_2$]; 2.0-2.1 [3s, 9H, 3×—COC$\underline{H}_3$]; 2.2-2.4 [dd, 2H, shik6-H,H']; 2.7-3.2 [m, 4H, —N(—C$\underline{H}_2$—CH$_2$—)$_2$; 2H, —N—C$\underline{H}_2$—CH$_2$—NH—CO; 2H, LysC$^\omega\underline{H}_2$]; 3.4-3.5 [m, 2H, —N—CH$_2$—C$\underline{H}_2$—NH—CO]; 4.3-4.4 [m, 1H, LysC$^\alpha\underline{H}$]; 4.7 [m, 1H, BOC—N$\underline{H}$]; 5.1-5.3 [m, 2H, shik-4-H, shik-5-H]; 5.6-5.7 [m, 1H, shik-3-H]; 6.4 [d, 1H, shik-2-H]; 7.1 [m, 1H, CO—N$\underline{H}$].

ES-MS: m/z=1162 [M+1]$^+$ for C$_{64}$H$_{117}$N$_6$O$_{12}$.

Step (vi): The intermediate VII prepared in above step (0.4 g, 0.35 mmol) was dissolved in 2 mL chloroform/methanol (1:1, v/v) and 5 mL methyl iodide was added to the solution. The reaction mixture was stirred at room temperature for 6 h and the solvent was removed on a rotary evaporator. The residue upon column chromatographic purification with silica gel (60-120 mesh size) and 2-2.5% methanol in dichloromethane (v/v) as eluent afforded 0.35 g (82% yield) of pure intermediate VIII. ($R_f$=0.45, 5% methanol in dichloromethane, v/v).

$^1$H NMR (300 MHz, CDCl$_3$): δ/ppm=0.9 [t, 6H, C$\underline{H}_3$—(CH$_2$)$_{13}$—]; 1.2-1.6 [m, 52H, 2×—(C$\underline{H}_2$)$_{13}$—, 4H, LysC$^\gamma\underline{H}_2$, 18H,CO—O—C(C$\underline{H}_3$)$_3$]; 1.65-2.0 [m, 4H, —N$^+$(—CH$_2$—C$\underline{H}_2$—)$_2$, 4H, LysC$^\delta\underline{H}_2$, LysC$^\beta\underline{H}_2$]; 2.0-2.15 [3s, 9H, 3×—COC$\underline{H}_3$]; 2.3-2.5 [dd, 1H, shik6-H,H']; 3.0-3.1 [m, 2H, LysC$^\omega\underline{H}_2$]; 3.3 [s, 3H, —N$^+$C$\underline{H}_3$]; 3.4-3.5 [m, 4H, —N$^+$(—C$\underline{H}$—CH$_2$—)$_2$]; 3.7-3.8 [m, 4H, —N$^+$—C$\underline{H}_2$—CH$_2$—NH—CO]; 4.4 [m, 1H, LysC$^\alpha\underline{H}$]; 4.8 [m, 1H, BOC—N$\underline{H}$] 5.1-5.3 [m, 2H, shik-4-H, shik-5-H]; 5.7 [t, 1H, shik-3-H]; 6.5-6.6 [d, 1H, shik-2-H].

ES-MS: m/z=1177 M+ for C$_{65}$H$_{120}$N$_6$O$_{12}$.

Step (vii): The intermediate VIII prepared above step (0.35 g, 0.3 mmol) was dissolved in 2 mL methanol and $K_2CO_3$ (0.2 g, 1.5 mmol) was added to the reaction mixture to increase the pH~9. The reaction mixture was allowed to stir at room temperature for 30 min, neutralized with Amberlite IR120 ($H^+$), filtered and the filtrate was dried over anhydrous sodium sulphate and concentrated on a rotary evaporator afforded 0.25 g (80% yield) of the intermediate IX. ($R_f$~0.6, 20% methanol-chloroform, v/v).

Step (viii): To the ice cold solution of the intermediate IX prepared in above step (0.25 g, 0.27 mmol) dissolved in 2 mL dry DCM 0.6 ml of TFA added and the mixture was allowed to stir for 3-4 h. TFA was removed by applying nitrogen, followed by the chloride ion exchange chromatography (using amberlyst A-26 chloride ion exchange resin). The final compound was recrystallized using MeOH & Acetone afforded 0.15 g (67% yield) of the pure target compound X (lipid 1) as a white solid. ($R_f$~0.3, 10% methanol-chloroform, v/v).

$^1$H NMR: (600 MHz, $CD_3OD+CDCl_3$): δ/ppm=0.9 [t, 6H, 2× C$\underline{H}_3$—$(CH_2)_{13}$—]; 1.2-1.5 [m, 52H, 2×—$CH_2(C\underline{H}_2)_{13}$—]; 1.6-2.0 [m, 6H, LysC$^γ\underline{H}_2$, LysC$^δ\underline{H}_2$, LysC$^β\underline{H}_2$, 4H, —$N^+$(—$CH_2$—$C\underline{H}_2$—)$_2$, 2H,]; 2.2 [dd, 1H, shik6-H]; 2.8 [dd, 1H, shik-6-H']; 2.9-3.2 [m, 2H, LysC$^ω\underline{H}_2$, 4H, —$N^+$(—$C\underline{H}_2$—$CH_2$—)$_2$]; 3.3-3.5 [m, 3H, —$N^+C\underline{H}_3$; 2H, —$N^+$—$CH_2$—$CH_2$—NH—CO]; 3.5-3.7 [m, 1H, shik4-H, 2H, —$N^+$—$CH_2$—$CH_2$—NH—CO]; 4.0-4.1 [m, 1H, shik-5-H]; 4.3-4.5 [m, 1H, LysC$^α\underline{H}$, 1H, shik3-H]; 6.5 [s, 1H, shik2-H].

ES-MS: m/z=850 [M]$^+$ and 425 [M/2]$^+$ for $C_{49}H_{98}N_6O_5$.

Example 2

Synthesis of the Cationic Amphiphile 2 (Scheme 2, Y, n=13)

Step (i): Solid HOBt (0.09 g, 0.67 mmol) and EDCI (0.13 g, 0.67 mmol) were added sequentially to an ice cold and stirred solution of 1,3,4,5-Tetraacetoxycyclohexane carboxylic acid (0.24 g, 0.67 mmol) in 5 mL dry DCM/dry DMF (9:1, v/v) under nitrogen atmosphere. After half an hour, the intermediate IV prepared as in scheme 1 (0.38 g, 0.51 mmol) was dissolved in dry DCM was added to the reaction mixture. The resulting solution was left stirred at room temperature overnight, diluted with excess DCM and washed sequentially with saturated sodium bicarbonate (~3× 50 mL) and water (~3×50 mL). The organic layer was dried over anhydrous sodium sulfate, filtered and the solvent from the filtrate removed by rotary evaporation. The residue upon column chromatographic purification with 60-120 mesh silica gel using 1.5-2% methanol in dichloromethane (v/v) as eluent afforded 0.31 g (56% yield) of the pure intermediate V. ($R_f$=0.5, 5% methanol in dichloromethane, v/v).

$^1$H NMR (300 MHz, $CDCl_3$): δ/ppm=0.9 [t, 6H, 2× C$\underline{H}_3$—$(CH_2)_{13}$—]; 1.2-1.7 [m, 56H, 2×—$C\underline{H}_2(C\underline{H}_2)_{13}$—; 9H,CO—O—C(C$\underline{H}_3$)$_3$; 4H, LysC$^γ\underline{H}_2$, LysC$^δ\underline{H}_2$]; 1.8-2.2 [m, 2H, LysC$^β\underline{H}_2$; 12H, 4× C$\underline{H}_3$]; 2.3-2.8 [m, 4H, qui6-H,H', qui2-H,H', 4H, —N(—$C\underline{H}_2$—$CH_2$—)$_2$, 2H, —N—C$\underline{H}_2$—$CH_2$—NHCO]; 3.0-3.3 [m, 2H, LysC$^ω\underline{H}_2$, 2H, —N—$CH_2$—$C\underline{H}_2$—NH—CO]; 4.4 [m, 1H, LysC$^α\underline{H}$]; 4.7 [m, 1H, BOC—N$\underline{H}$]]; 4.9-5.1 [dd, 1H, qui4-H]; 5.3-5.45 [ddd, 1H, qui5-H]; 5.5-5.6 [m, 1H, qui3-H].

ES-MS: m/z: 1080 [M+1]$^+$ for $C_{60}H_{110}N_4O_{12}$.

Step (II): The intermediate V (0.5 g, 0.5 mmol) prepared in above step was dissolved in dry DCM (4 mL) and TFA (2 mL) was added at 0° C. The resulting solution was left stirred at 0° C. for 3 h to ensure complete deprotection.

Excess TFA was removed by nitrogen flushing. The resulting compound was dissolved in chloroform (80 mL) and washed with aqueous saturated $NaHCO_3$ (3×90 mL), brine (1×70 mL). The organic layer was dried over anhydrous sodium sulfate, filtered and the solvent from the filtrate removed by rotary evaporation afforded 0.41 g (91% yield) of free amine as intermediate VI.

Step (III): Mercury chloride (0.28 g, 1.0 mmol) was added to a mixture of intermediate VI (prepared in step II, 0.4 g. 0.4 mmol), bis-N-Boc-thiourea (0.2 g, 0.7 mmol) dissolved in dry N,N-dimethylformamide (DMF, 2 mL), Triethylamine (1 mL) and dry dichloromethane (DCM, 5 mL) at 0° C. with continuous stirring. The resulting mixture was stirred at 0° C. under nitrogen for 40 min, diluted with ethyl acetate (20 mL), and filtered through a pad of Celite. The filtrate was sequentially washed with water (2×50 mL) and brine solution (2×50 mL), dried over anhydrous sodium sulfate, and filtered, and the solvent from the filtrate was removed by rotary evaporation. The residue upon column chromatographic purification with 60-120 mesh silica gel using 2-2.5% methanol/dichloromethane (v/v) as eluent afforded 0.41 g of the pure intermediate VII (71%, Rf–0.5, 5% methanol/dichloromethane, v/v).

$^1$H NMR (300 MHz, $CDCl_3$): δ/ppm=0.9 [t, 6H, 2× C$\underline{H}_3$—$(CH_2)_{13}$—]; 1.2-1.7 [m, 56H, 2×—$C\underline{H}_2(C\underline{H}_2)_{13}$—; 18H,CO—O—C(C$\underline{H}_3$)$_3$; 4H, LysC$^γ\underline{H}_2$, LysC$^δ\underline{H}_2$]; 1.8-2.2 [m, 2H, LysC$^β\underline{H}_2$; 12H, 4× C$\underline{H}_3$]; 2.3-2.8 [m, 4H, qui6-H,H', qui2-H,H', 4H, —N(—$C\underline{H}_2$—$CH_2$—)$_2$, 2H, —N—C$\underline{H}_2$—$CH_2$—NHCO]; 3.0-3.3 [m, 2H, LysC$^ω\underline{H}_2$, 2H, —N—$CH_2$—$C\underline{H}_2$—NH—CO]; 4.4 [m, 1H, LysC$^α\underline{H}$]; 4.7 [m, 1H, BOC—N$\underline{H}$]]; 4.9-5.1 [dd, 1H, qui4-H]; 5.3-5.45 [ddd, 1H, qui5-H]; 5.5-5.6 [m, 1H, qui3-H].

ES-MS: m/z=1221 [M+1]$^+$ for $C_{66}H_{121}N_6O_{13}$.

Step (iv): The intermediate VII prepared in above step (0.3 g, 0.29 mmol) was dissolved in 2 mL chloroform/methanol (1:1, v/v) and 5 mL methyl iodide was added to the solution. The reaction mixture was stirred at room temperature for 6 h and the solvent was removed on a rotary evaporator. The residue upon column chromatographic purification with silica gel (60-120 mesh size) and 2-2.5% methanol in dichloromethane (v/v) as eluent afforded 0.18 g (58% yield) of pure intermediate VIII. ($R_f$=0.45, 5% methanol in dichloromethane, v/v).

$^1$H NMR (300 MHz, $CDCl_3$): δ/ppm=0.9 [t, 6H, 2× C$\underline{H}_3$—$(CH_2)_{13}$—]; 1.2-1.5 [m, 52H, 2×—$CH_2(C\underline{H}_2)_{13}$—; 18H, CO—O—C(C$\underline{H}_3$)$_3$]; 1.6-1.9 [4H, —N(—$CH_2$—$C\underline{H}_2$—)$_2$; 6H, LysC$^γ\underline{H}_2$, LysC$^δ\underline{H}_2$, LysC$^β\underline{H}_2$]; 2.0-2.3 [4s, 12H, 4× $CH_3$]; 2.4-2.7 [dd, 2H, qui6-H,H'; dd, 2H, qui2-H, H']; 3.1 [d, 2H, LysC$^ω\underline{H}_2$]; 3.2 [s, 3H, $N^+CH_3$]; 3.3-3.4 [m, 4H, —$N^+$(—$C\underline{H}_2$—$CH_2$—)$_2$]; 3.6- 3.8 [m, 4H, —$N^+$—C$\underline{H}_2$—$CH_2$—NHCO]; 4.3-4.4 [m, 1H, LysC$^α\underline{H}$]; 4.9-5.1 [m, 1H, BOC—N$\underline{H}$; 1H, qui4-H]; 5.3-5.45 [ddd, 1H, qui5-H]; 5.5-5.6 [d, 1H, qui3-H].

ES-MS: m/z: 1236 [M]$^+$ for $C_{67}H_{124}N_6O_{13}$.

Step (v): The intermediate VIII prepared above step (0.18 g, 0.2 mmol) was dissolved in 2 mL methanol and $K_2CO_3$ (0.1 g, 1.5 mmol) was added to the reaction mixture to increase the pH~9. The reaction mixture was allowed to stir at room temperature for 30 mins, neutralized with Amberlite IR120 ($H^+$), filtered and the filtrate was dried over anhydrous sodium sulphate. The solvent was removed by rotary evaporator afforded 0.11 g (72% yield) of the intermediate IX. ($R_f$~0.6, 20% methanol-chloroform, v/v).

Step (vi) & (vii): To the ice cold solution of the intermediate IX prepared in above step (0.1 g, 0.06 mmol) was dissolved in 2 mL dry DCM 0.6 ml of TFA added and the mixture was allowed to stir for 3-4 h. TFA was removed by applying nitrogen, followed by chloride ion exchange chromatography (using amberlyst A-26 chloride ion exchange resin). The final compound was recrystallized using MeOH & Acetone afforded 0.08 g (75% yield) of the pure target compound Y as a white solid. ($R_f$=~0.3, 10% methanol-chloroform, v/v).

$^1$H NMR: (600 MHz, $CD_3OD+CDCl_3$): δ/ppm=0.9 [t, 6H, $CH_3$—$(CH_2)_{13}$—]; 1.2-1.5 [m, 52H, {—$CH_2(CH_2)_{13}$—$}_2$; 2H, LysC$^δ$$H_2$]; 1.65-2.2 [m, 4H, —$N^+$(—$CH_2$—$CH_2$—$)_2$; 2H, LysC$^β$$H_2$, LysC$^γ$$H_2$; 2H, qui6-H,H'; 2H, qui2-H,H']; 2.9-3.7 [m, 4H, —$N^+$(—$CH_2$—$CH_2$—$)_2$; 3H, —$N^+CH_3$; 2H, LysC$^ω$$H_2$; 4H, —$N^+$—$CH_2$—$CH_2$—NH—CO; 1H, qui4-H]; 4.0-4.2 [m, 2H, qui-3H, qui-5H]; 4.4 [m, 1H, LysC$^α$$H$].

ES-MS: m/z: 868 [M]$^+$ 434 [M/2]$^+$ for $C_{49}H_{100}N_6O_6$.

Example 3

Synthesis of Control Mannosylated Lipid 3 (Scheme 3):

Step (i): Solid HOBt (0.36 g, 2.3 mmol) and EDCI (0.45 g, 2.3 mmol) were added sequentially to an ice cold and stirred solution of 2-(tert-butyldiphenylsilyloxy)acetic acid (0.74 g, 2.3 mmol) in 5 mL dry DCM/dry DMF (9:1, v/v) under nitrogen atmosphere. After half an hour, intermediate N-2-[(N$^ε$—Z-L-Lysyl)]aminoethyl-N,N-di-n-hexadecylamine (1.2 g, 1.5 mmol, prepared as described in Pramanik, D. et al. J Med Chem. 2008; 51:7298-7302) was dissolved in dry DCM was added to the reaction mixture. The resulting solution was left stirred at room temperature overnight, diluted with excess chloroform and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 60-120 mesh silica gel using 1-1.5% methanol in chloroform (v/v) as eluent afforded 1.6 g (73% yield) of the pure intermediate III. ($R_f$=0.5, 5% methanol in dichloromethane, v/v).

$^1$H NMR (300 MHz, $CDCl_3$): δ/ppm=0.9 [t, 6H, 2× $CH_3$—$(CH_2)_{13}$—]; 1.0-1.1 [m, 9H, —$C(CH_3)_3$]; 1.2-1.5 [m, 52H, 2×—$(CH_2)_{13}$; 4H, —N(—$CH_2$—$CH_2$—$)_2$; 4H, LysC$^γ$$H_2$, LysC$^δ$$H_2$]; 1.8-1.9 [m, 2H, LysC$^β$$H_2$]; 2.4-2.5 [t, 4H, —N(—$CH_2$—$CH_2$—$)_2$ ]; 2.5-2.6 [t, 2H, —N—$CH_2$—$CH_2$—NH—CO]; 3.0-3.2 [m, 2H, LysC$^ω$$H_2$]; 3.25-3.4 [m, 2H, —N—$CH_2$—$CH_2$—NH—CO]; 4.0- 4.1 [s, 2H, —$CH_2$—O—Si—]; 4.3-4.4 [m, 1H, LysC$^α$$H$]; 4.9-5.0 [m, —$CH_2$—$C_6H_5$; —$CH_2$—O—Si—]; 7.2-7.7 [m, 15H, —$(C_6H_5)_3$].

ES-MS: m/z: 1069 [M+2]$^+$ for $C_{66}H_{110}N_4O_5Si$.

Step (ii): The intermediate III prepared in above step (1.2 g, 1.5 mmol) was dissolved in dry THF and tertiary butyl ammonium fluoride (0.6 g, 2.3 mmol) was slowly added at 0° C. The resultant solution left stirred at room temperature for 2 h, diluted with excess chloroform and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 60-120 mesh silica gel using 1.5-2% methanol in chloroform (v/v) as eluent afforded 1 g (80% yield) of the pure intermediate IV. ($R_f$=0.3, 5% methanol in chloroform, v/v).

$^1$H NMR (300 MHz, $CDCl_3$): δ/ppm=0.9 [t, 6H, $CH_3$—$(CH_2)_{11}$—]; 1.0-2.0 [m, 52H, —$(CH_2)_{13}$; 4H, —N—$CH_2$—$CH_2$—$)_2$; 6H, LysC$^γ$$H_2$, LysC$^δ$$H_2$, LysC$^β$$H_2$]; 2.9-3.1 [m, 4H, —N(—$CH_2$—$CH_2$—$)_2$; 2H, LysC$^ω$$H_2$; 2H, —N—$CH_2$—$CH_2$—NH—CO]; 3.4-3.6 [m, 2H, —N—$CH_2$—$CH_2$—NH—CO]; 3.9-4.3 [m, 2H, —$CH_2$—O—Si—; 1H, LysC$^α$$H$]; 5.0-5.2 [m, —$CH_2$—$C_6H_5$; —$NHZ$]; 7.2-7.7 [m, 15H, —$(C_6H_5)_3$].

ES-MS: m/z: 830 [M+1]$^+$ for $C_{50}H_{92}N_4O_5$.

Step (iii): The intermediate IV prepared in above step (0.9 g, 0.93 mmol) and the intermediate prepared from mannose (0.7 g, 1.4 mmol, prepared as before Srinivas, R. et al J. Med. Chem. 2010; 317:992-999) were dissolved in dry DCM under nitrogen atmosphere and boron trifluoride ethyletherate (0.2 g, 1.4 mmol) was added at −20° C. The resultant solution left stirred at −20° C. for 2 hr, diluted with excess chloroform and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 100-200 mesh silica gel using 1-1.5% methanol in chloroform (v/v) as eluent afforded 0.5 g (51% yield) of the pure intermediate V. ($R_f$=0.5, 5% methanol in chloroform, v/v).

$^1$H NMR (300 MHz, $CDCl_3$): δ/ppm=0.9 [t, 6H, ($CH_3$—$(CH_2)_{13}$—$)_2$]; 1.2-1.9 [m, 52H, —$(CH_2)_{13}$; 4H, —N(—$CH_2$—$CH_2$—$)_2$; 6H, LysC$^δ$$H_2$, LysC$^β$$H_2$, LysC$^γ$$H_2$]; 2.0-2.2 [4s, 12H, 4×—CO—$CH_3$]; 2.5-2.8 [m, 4H, —N(—$CH_2$—$CH_2$—$)_2$; 2H, —N—$CH_2$—$CH_2$—NH—CO]; 3.1-3.4 [m, 2H, LysC$^ω$$H_2$]; 2H, —N—$CH_2$—$CH_2$—NH—CO; 3H, 5-H]; 4.0-4.4 [m, 2H, —NH—CO—$CH_2$—O—; 2H, —$CH_2$—$OCOH_3$, 1H, LysC$^α$$H$]; 4.8 [s, 1H, 1-H]; 5.0 [s, —$CH_2$—$C_6H_5$]; 5.2-5.4 [m, 3H, 2-H, 3-H, 4-H]; 7.2-7.7 [m, 5H, —$(C_6H_5)$].

ES-MS: m/z: 1160 [M+1]$^+$ for $C_{64}H_{110}N_4O_{14}$.

Step (iv): The intermediate V prepared in above step (0.5 g, 0.4 mmol) was dissolved in 8 mL methanol and 2 drop of 2N hydrochloric acid. Pd(OH)$_2$/C (0.2 g) was added to the reaction mixture and air was removed. The resultant reaction mixture was stirred at room temperature for 14 h under hydrogen atmosphere (2 atmos). The reaction mixture was filtered using celite and the filtrate was dried over anhydrous sodium sulphate and the solvent from the filtrate removed by rotary evaporation afforded the 0.4 g (90% yield) of pure intermediate VI. ($R_f$=~0.4, 10% methanol-chloroform, v/v).

Step (V): Mercury chloride (0.28 g, 1.0 mmol) was added to a mixture of intermediate VI (prepared in step IV, 0.4 g. 0.45 mmol), bis-N-Boc-thiourea (0.2 g, 0.7 mmol) dissolved in dry N,N-dimethylformamide (DMF, 2 mL), Triethylamine, (1 mL) and dry dichloromethane (DCM, 5 mL) at 0° C. with continuous stirring. The resulting mixture was stirred at 0° C. under nitrogen for 40 min, diluted with ethyl acetate (20 mL), and filtered through a pad of Celite. The filtrate was sequentially washed with water (2×50 mL) and brine solution (2×50 mL), dried over anhydrous sodium sulfate, and filtered, and the solvent from the filtrate was removed by rotary evaporation. The residue upon column chromatographic purification with 60-120 mesh silica gel using 2-2.5% methanol/dichloromethane (v/v) as eluent afforded 0.41 g of the pure intermediate VII (71%, Rf=0.5, 5% methanol/dichloromethane, v/v).

$^1$H NMR (300 MHz, $CDCl_3$): δ/ppm=0.9 [t, 6H, ($CH_3$—$(CH_2)_{13}$—$)_2$]; 1.2-1.9 [m, 52H, —$(CH_2)_{13}$; 4H, —N(—$CH_2$—$CH$—$)_2$; 6H, LysC$^δ$$H_2$, LysC$^β$$H_2$, LysC$^γ$$H_2$; 18H, CO—O—$C(CH_3)_3$]; 2.0-2.2 [4s, 12H, 4×—CO—$CH_3$]; 2.5-2.8 [m, 4H, —N(—$CH_2$—$CH_2$—$)_2$; 2H, —N—$CH_2$—$CH_2$—NH—CO]; 3.1-3.4 [m, 2H, LysC$^ω$$H_2$]; 2H, —N—$CH_2$—$CH_2$—NH—CO; 3H, 5-H]; 4.0-4.4 [m, 2H, —NH—CO—CH$_2$—O—; 2H, —CH$_2$—OCOCH$_3$, 1H, LysC$^\alpha$H]; 4.8 [s, 1H, 1-H]; 5.2-5.4 [m, 3H, 2- H, 3-H, 4-H].

ES-MS: m/z: 1267 [M+1]$^+$ for C$_{67}$H$_{123}$N$_6$O$_{16}$.

Step (vi): The intermediate VII prepared in above step (0.2 g, 0.15 mmol) was dissolved in 3 mL chloroform and 10 mL methyl iodide was added to the solution. The reaction mixture was stirred at room temperature for overnight and the solvent was removed on a rotary evaporator. The residue upon column chromatographic purification with silica gel (60-120 mesh size) and 2-2.5% methanol in chloroform (v/v) as eluent afforded 0.15 g (82% yield) of pure intermediate VIII. (R$_f$=0.4, 5% methanol in chloroform, v/v).

$^1$H NMR (300 MHz, CDCl$_3$): δ/ppm=0.9 [t, 6H, 2× CH$_3$—(CH$_2$)$_{13}$—]; 1.2-1.5 [m, 52H, 2×—(CH$_2$)$_{13}$; 2H, LysC$^\gamma$H$_2$]; 1.7-1.9 [m, 4H, —N$^+$(—CH$_2$—CH$_2$—)$_2$; 2H, LysC$^\beta$H$_2$, 2H, LysC$^\delta$H$_2$; 18H, CO—O—C(CH$_3$)$_3$]; 2.0-2.2 [4s, 12H, 4×—CO—CH$_3$]; 3.1-3.5 [m, 3H, —N$^+$—CH$_3$; 2H, LysC$^\omega$H$_2$; 4H—N$^+$(—CH—CH$_2$—)$_2$; 1H, 5-H]; 3.6-3.8 [m, 4H, —N$^+$—CH$_2$—CH$_2$—NH—CO—]; 4.0-4.4 [m, 2H, —NH—CO—CH$_2$—O—; 2H, —CH$_2$—OCOCH$_3$]; 4.5 [dd, 1H, LysC$^\alpha$H]; 4.8 [s, 1H, 1-H]; 5.2-5.4 [m, 3H, 2-H, 3-H, 4-H].

ESI-MS: m/z: 1282 [M]$^+$ for C$_{68}$H$_{126}$N$_6$O$_{16}$.

Step (vii): The intermediate VIII prepared above step (0.15 g, 0.2 mmol) was dissolved in 2 mL methanol and K$_2$CO$_3$ (0.1 g, 1.5 mmol) was added to the reaction mixture to increase the pH~9. The reaction mixture was allowed to stir at room temperature for 30 mins, neutralized with Amberlite IR120 (H$^+$), filtered and the filtrate was dried over anhydrous sodium sulphate. The solvent was removed by rotary evaporator afforded 0.1 g (75% yield) of the intermediate IX. (R$_f$~0.6, 20% methanol-chloroform, v/v).

Step (viii): To the ice cold solution of the intermediate IX prepared in above step (0.1 g, 0.06 mmol) was dissolved in 2 mL dry DCM 0.6 ml of TFA added and the mixture was allowed to stir for 3-4 h. TFA was removed by applying nitrogen, followed by chloride ion exchange chromatography (using amberlyst A-26 chloride ion exchange resin). The final compound was recrystallized using MeOH & Acetone afforded 0.08 g (75% yield) of the pure target compound 3 as a white solid. (R$_f$~0.2, 20% methanol-chloroform, v/v).

$^1$H NMR: (600 MHz, CDCl$_3$+CD$_3$OD): δ/ppm=0.9 [t, 6H, 2× CH$_3$—(CH$_2$)$_{13}$—]; 1.2-1.5 [m, 52H, 2×—(CH$_2$)$_{13}$]; 1.5-1.9 [4H, —N$^+$(—CH$_2$—CH$_2$—)$_2$; 6H, LysC$^\beta$H$_2$, LysC$^\gamma$H$_2$, LysC$^\delta$H$_2$]; 2.9-3.1 [m, 2H, LysC$^\omega$H$_2$; 3H, —N$^+$—CH$_3$; 4H —N$^+$(—CH$_2$—CH$_2$—)$_2$; 2H, —N$^+$—CH—$_2$CH$_2$—NH—CO—]; 3.5-4.0 [4H, 2-H, 3-H, 4-H, 5-H; 2H, —CH$_2$—OH; 2H, —N$^+$—CH$_2$—CH$_2$—NH—CO—]; 4.0-4.4 [m, 2H, —NH—CO—CH$_2$—O—; 1H, LysC$^\alpha$H]; 4.9 [s, 1H, 1-H].

ES-MS: m/z: 954 [M]$^+$ 457 [M/2]$^+$ for C$_{50}$H$_{103}$N$_6$O$_8$.

Example 4

Evaluation of the mannose receptor specific gene transfer efficacies of cationic amphiphiles 1-3 in Dendritic cells.

Preparation of Plasmid DNA.

pCMV-SPORT-β-gal, p-CMV-Tyrosinase & p-CMV-gp100 were purchased from RAS Life Sciences, Hyderabad, India. Plasmids were amplified in DH5α-strain of *Escherichia coli*, isolated by alkaline lysis procedure and finally purified by PEG-8000 precipitation as described previously (Karmali P P, et al. J Med Chem. 2004; 47:2123-2132). The purity of plasmid was checked by A$_{260}$/A$_{280}$ ratio (around 1.9) and 1% agarose gel electrophoresis.

Preparation of Liposomes.

The liposomes were prepared by the conventional method. Briefly, lipids and co-lipids (Cholesterol, DOPE, DOPC) at appropriate molar ratios were dissolved in chloroform. The solvent was then evaporated under a thin stream of nitrogen gas, vacuum dried for 8 h and hydrated in deionised water overnight to give a final lipid concentration of 1 mM for in vitro experiments or 5 mM for in vivo experiments. The hydrated lipid film was first vortexed for 30 seconds and then sonicated until clarity using a Branson 450 sonifier at 100% duty cycle and 25 W output power. The resulting clear aqueous liposomes were used in preparing lipoplexes.

Isolation of Dendritic Cells.

Primary mbmDCs were isolated using a previously described procedure (Inaba K, et al. J Exp Med 1992; 176:1693-1702). Briefly, bone marrow collected from tibias and fibulas of male C57BL/6 mice was passed through a nylon mesh to remove bone and debris, and resuspended in complete DC medium (RPMI-1640 containing 10% FBS, 50 μM β-mercaptoethanol, 2 mM glutamine, 1% NEAA, 20 ng/mL GM-CSF and 10 ng/mL IL-4, 1% antibiotic solution). Cells were supplemented with fresh DC medium every two days. After 6 days, the aggregated cells were dislodged by gently pipetting RPMI over the adherent stroma. The dislodged cells were pulled together and centrifuged at 280 g for 10 min at room temperature. The supernatant was discarded. The pellets were first resuspended in complete DC medium at 1×10$^6$ cells/mL and finally placed in 100 mm cell culture petri dishes at 1×10$^7$ cells/dish in 10 mL medium per dish. After 24 h, the nonadherent cells were collected by gently swirling the dish and were used for transfection and flow cytometry experiments. Cultures were maintained in a humidified atmosphere with 5% CO$_2$ at 37° C.

DC-Transfection.

Figure 5:
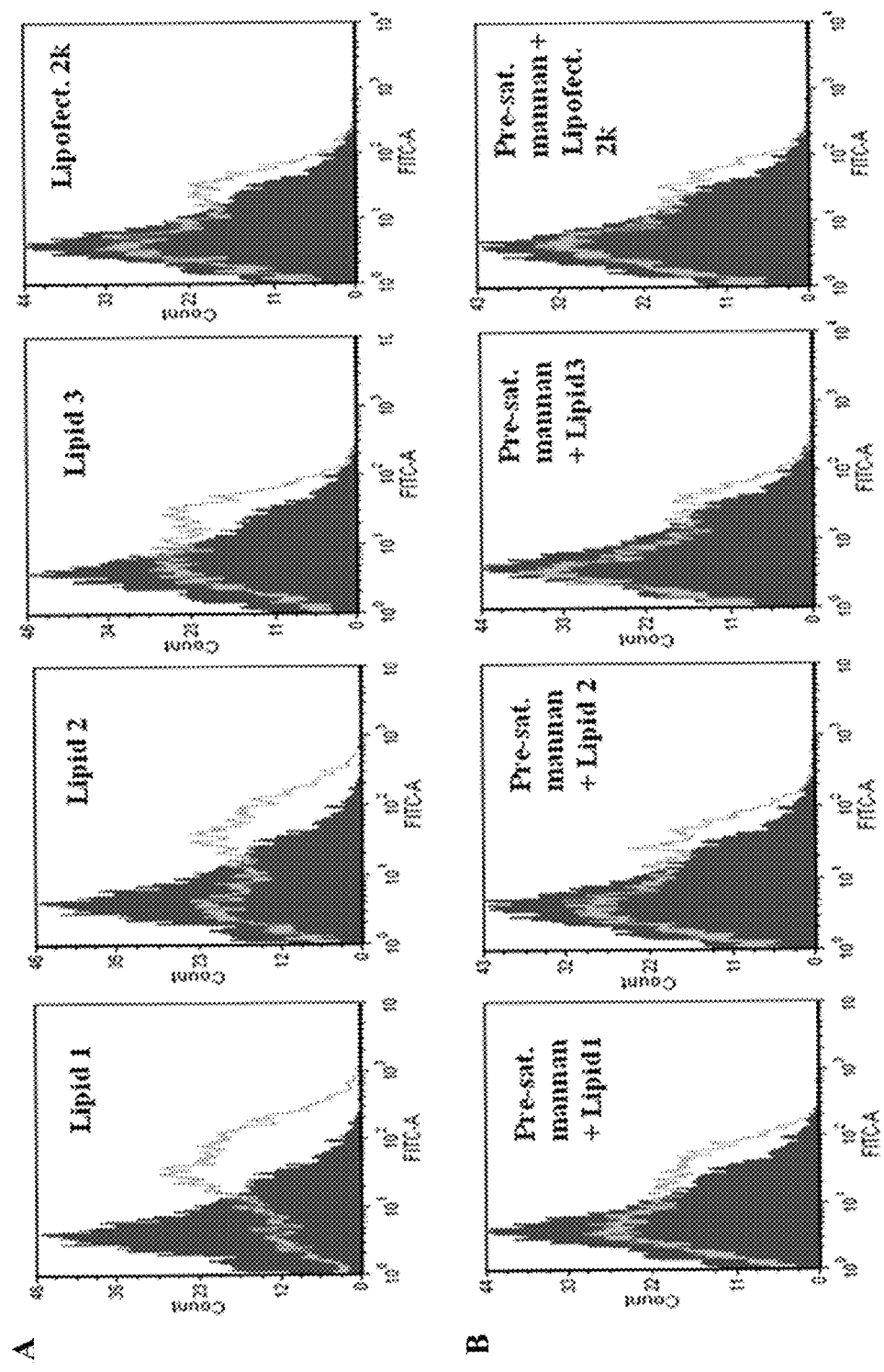
FIG. 5 shows that mbm-DC transfection efficiencies of 1 & 2 are mediated by mannose receptors and are higher than that of their mannosyl analog 3. The degrees of GFP expression in mbmDCs transfected with lipoplexes of lipids 1-3 and α5-GFP plasmids were measured by flow cytometry. A) transfection efficiencies in mbmDCs; B) transfection efficiencies in mbmDCs pre-saturated with mannan (1 mg/mL); In each of these transfection experiments, ~$5 \times 10^5$ cells were used and the cells were transfected with lipoplexes containing lipid:DNA charge ratios of 8:1. For comparison sake, the transfection efficiencies in each case were also measured using GFP lipoplexes of the commercially available liposomal transfection kit, LipofectAmine 2000 (shown in the extreme right panels in sections A & B). Each experiment was repeated three times and similar transfection profiles were observed in each time.

First, the transfection efficiency of the lipids 1, 2 & 3 were evaluated in mouse bone marrow derived dendritic cells. To this end, the immature dendritic cells were isolated from the bone marrow of C57BL/6J mice by culturing with GM-CSF and IL-4 following the protocol described above. The immature dendritic cells were characterized for the standard DC-markers including MHC Class II, CD86, CD11c, CD40 and mannose receptors by treating the DCs with FITC/PE conjugated monoclonal antibodies for these DC markers. The profiles of the DC markers were monitored by flow cytometry. Findings in flow cytometry confirmed the characteristics of immature DCs having high intracellular levels of MHC class II molecules, low CD 86, high levels of CD11c, CD 40 and mannose receptor (FIG. 4). After confirming the presence of these expected DC markers on the surface of the isolated DCs, the transfection efficiencies of the cationic amphiphiles 1, 2 & 3 were evaluated in mbm-DCs. The isolated DCs were seeded in 6 well plates with 1×10$^6$ cells per well. Lipoplexes containing 3 μg of plasmid DNA encoding green fluorescence protein (pα5GFP) and 8 nmol cationic amphiphiles 1, 2 & 3 were added to the cells and incubated for 4 h at 37° C. in serum free medium with 5% CO$_2$. After 4 h incubation, medium was replaced with complete DC medium and incubated for 18 h at 37° C. in presence of 5% CO$_2$. The transfection efficiencies of the cationic amphiphiles 1, 2 & 3 were measured by Flow cytometric analysis. The findings summarized in FIG. 5 clearly demonstrate that the efficacies of cationic amphiphiles 1 & 2 in delivering genes to dendritic cells are superior to those of their mannosyl analog 3.

Example 6

Induction of humoral and cellular immune responses in dendritic cell based genetic immunizations.

Mice Immunization. 6-8 weeks old female C57BL/6 mice (each weighing 20-22 g, n=5) were immunized by subcutaneous administration of only lipoplex of lipids 1-3 and p-CMV-β-gal or lipid 1 & p-CMV-Gp-100; 1 & p-CMV-Tyrosinase (150 µl in 5% glucose solution, 15 µg DNA, 4:1 lipid:DNA ratio), three times with a seven-day interval. Two weeks after the third immunization, mice were sacrificed and sera & spleens were collected for immune response assays or challenged with B16F1 melanoma cells.

Example 7

Measurement of anti β-gal antibody by ELISA assay (humoral response). Anti-β-gal antibodies were measured using an enzyme linked immunosorbent (ELISA) assay as described earlier (McKeever, U. et al. Vaccine 2002; 20:1524-1531). Briefly, 96 well ELISA plates were coated with β-gal protein (0.3 µg per well) using a 5 µg/mL stock solution prepared in PBS. Plates were washed with PBS (3×200 µL) and blocked with 1% BSA in PBS at room temperature for 2 h. The plates were then washed with PBS containing 0.05% Tween-20 (3×200 µL) and incubated with mouse sera (100 µL) at room temperature for 2 h. The plates were again washed with PBS containing 0.05% Tween-20 (3×200 µL) and 100 µL of diluted (1:1000) anti-mouse antibody conjugated to horse radish peroxidase was added to each well. The plates were incubated at room temperature for 2 h and the unbound antibody-HRP conjugate was removed by washing the plates with PBS containing 0.05% Tween-20 (3×200 µL). The plates were then incubated in dark with 100 µL of ABTS (Calbiochem, USA) per well at room temperature for 10 min and the absorbance was measured at 405 nm by ELISA reader (Bio-Tek instruments Inc, UK). The findings summarized in Part A, FIG. 6 demonstrate that administration of DCs pre transfected with liposomes of cationic amphiphiles 1 & 2 elicited higher anti β-gal antibody responses than in case of administration of DCs pre-transfected with liposomes of the mannosyl analog 3. Stated differently, the findings summarized in Part A, FIG. 6 convincingly demonstrate that the immunization of mice with DCs pre-transfected with the complex of model DNA vaccine and liposomes of the presently disclosed cationic amphiables is capable of eliciting efficient antigen specific humoral immune response against the antigen encoded in the model DNA vaccine.

Example 8

In situ IFN-γ (cellular immune response) and IL-4 (humoral immune response) by ELISA assays. CD4+ Th cells exhibit their helper functions through secreted cytokines. Differences in cytokine secretion patterns among the two Th cell subsets (Th1 and Th2) determine the type of immune response mounted against a particular antigenic challenge. Th1 subset is responsible for mounting cell-mediated immune response e.g. activation of $T_C$ cells, while Th2 subset stimulates humoral responses, e.g. activation of antibody producing B cells. Two defining cytokines secreted by Th1 and Th2 cells are interferon gamma (INF-γ) and interleukin-4 (IL-4), respectively (Rengarajan, J. et al. Immunology Today 2000; 21:479-483). IFN-γ and IL-4 ELISA assays were performed as described previously (McKinney D M, et al. Journal of Immunological Methods 2000; 237:105). Two weeks after the last immunization, mice were sacrificed and their spleens were collected. Splenocytes were isolated by mincing the spleens with a syringe plunger and the erythrocytes were lysed with 1 mL of lysis buffer (0.14 M ammonium chloride in 0.02 M Tris.HCl, pH 7.2). The viable cells were counted by hemocytometer and used for Interferon-γ and IL-4 ELISA assays immediately (without any in vitro restimulation). The assay was performed according to manufacturer's protocol (Endogen Mouse IFN-γ Elisa kit, and mouse IL-4 Elisa kit, Pierce Biotechnology, USA). Briefly, splenocytes were incubated in 96-well plates pre-coated with anti-mouse IFN-γ or anti-mouse IL-4 antibodies at $1 \times 10^6$ cells/well in 50 µL complete medium. The plates were covered and incubated for 12 h at 37° C. in presence of 5% $CO_2$. The cells were then washed out with wash buffer (3×200 µL) and 50 µL of the biotinylated secondary antibody was added to each well and incubated for 1 h at room temperature. The plates were washed with wash buffer (3×200 µL) and incubated with 100 µL of streptavidin-HRP solution for 30 min. The plates were again washed with wash buffer (3×200 µL), treated with 100 µL of TMB substrate solution and incubated for 30 min in dark. The reaction was stopped by adding 100 µL of stop solution and the absorbance was measured on a microplate reader at 450 nm.

Example 9

Tumor Challenge Experiment.

B16F1 melanoma cells were harvested from T25 culture flasks using 1 mL cell dissociation solution (Sigma, USA), washed PBS (2×500 µL) and resuspended at $5 \times 10^5$ cells/mL in HBSS. Two weeks after the last immunization, $1 \times 10^5$ B16F1 cells in 200 µL HBSS were injected (s.c.) into 6-8 weeks old female C57BL6/J mice (n=5). Two weeks later, visual inspection and palpation were carried out to detect tumors and when tumors appeared, daily measurements of perpendicular tumor diameters were made. Mice were euthanized if any measurement exceeded 14.

Advantage of the Present Invention

The process of the present invention can be exploited for preparing cationic amphiphiles with mannose-mimicking cationic amphiphiles and for delivering biologically active compounds such as DNA, RNA, proteins, etc. into antigen presenting cells in genetic immunization. The present inventions are particularly useful for mannose receptor specific delivery of polyanions, polypeptides or nucleopolymers into the antigen presenting cells. The present invention is directed to methods of eliciting immune responses in animals through administering complexes of liposomes prepared with presently described cationic amphiphiles and a polynucleotide coding for an antigenic determinant. Furthermore, the present invention is also directed to methods of eliciting active immunity against an infectious disease in animals through administering complexes of the presently described cationic amphiphiles and a polynucleotide coding for the infectious disease causing protein. The present invention is also related to the genetic immunization methods wherein the polynucleotide is an expression vector comprising a DNA sequence encoding the antigenic determinant of the infectious disease causing immunogen and wherein the transcription of the DNA is under the control of a promoter. The present invention is further directed to a genetic immunization wherein the polynucleotide is an RNA molecule encoding for an infectious immunogen. In particular, the presently disclosed novel cationic amphiphiles with mannose-mimicking shikimic and quinic acid head-groups hold potential for future exploitation in genetic immunization in delivering DNA or RNA encoding infectious immunogen. The another distinguishing feature of the present invention is that the efficiencies of the novel cationic amphiphiles disclosed herein in transfecting dendritic cells, the most professional antigen presenting cells, is ~4-5 fold superior to those of the first generation cationic amphiphiles with shikimic and quinic acid head-groups recently disclosed by Srinivas, R. et al. J. Med. Chem. 2010; 53:1387-1391. Most important embodiment of the invention is inducing long-lasting tumor protection after challenging the immunized mice with lethal dose of aggressive melanoma tumor. The findings disclosed in the present invention avoid the needs of (a) painstaking and costly isolation of autologous dendritic cells; (b) ex-vivo transfection of the isolated DCs with DNA vaccines and (c) the re-implantation of the transfected DCs back into the recipients body. Taken together, the present invention is going to make genetic immunization simple and cost-effective.

We claim:

1. A cationic amphiphile compound of formula I

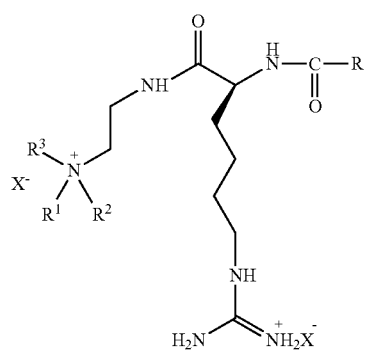

Formula I wherein R is selected from the group consisting of shikimoyl, quinoyl, and mannosyl group,

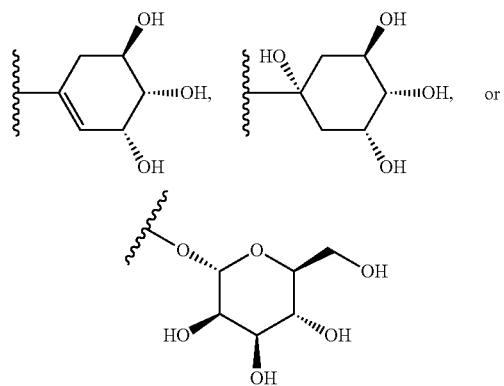

$R^1$ and $R^2$ are each independently hydrogen or a lipophilic moiety and $R^1$ and $R^2$ are not hydrogen at the same time;

$R^3$ is independently hydrogen, $C_1$-$C_5$ alkyl, $C_1$-$C_5$ hydroxy alkyl and $C_1$-$C_5$ amino alkyl;

X is optionally selected from chlorine or bromine;

wherein lipophilic moiety is selected from the group consisting of $C_{8-24}$ alkyl, mono-, di- and tri-unsaturated alkenyl.

2. The compound as claimed in claim 1, wherein the compound is selected from the group consisting of:

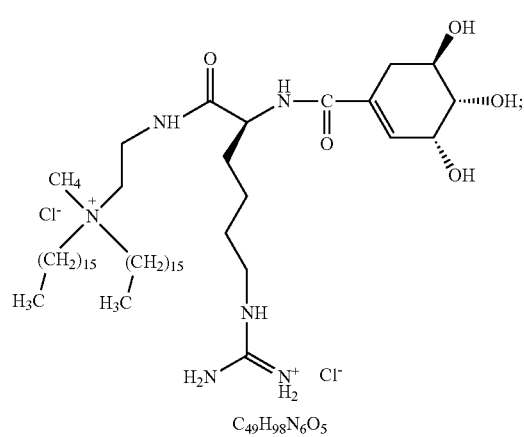

$C_{49}H_{98}N_6O_5$

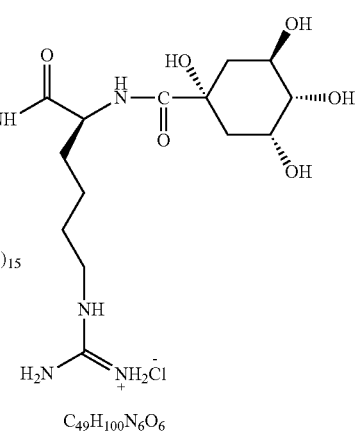

$C_{49}H_{100}N_6O_6$

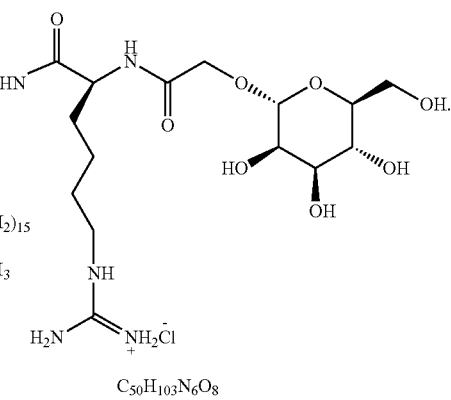

$C_{50}H_{103}N_6O_8$

3. The compound as claimed in claim 1, wherein the compound is for use in in-vivo delivery of DNA vaccine.

4. A process for the preparation of compounds of formula I,

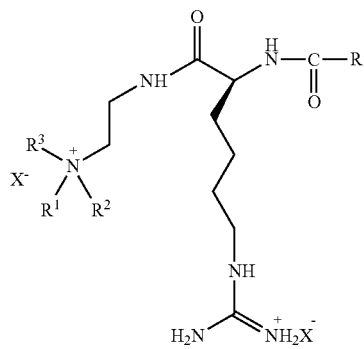

Formula I wherein R is selected from the group consisting of shikimoyl, quinoyl, and mannosyl group,

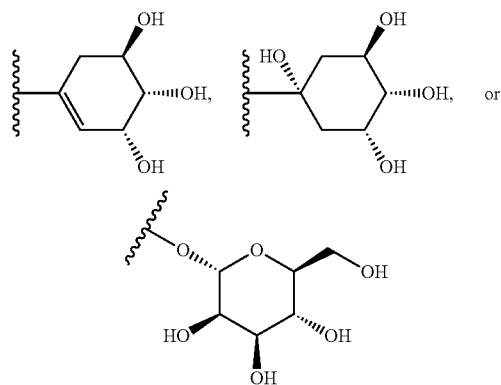

$R^1$ and $R^2$ are each independently hydrogen or a lipophilic moiety and $R^1$ and $R^2$ are not hydrogen at the same time;
$R^3$ is independently hydrogen, $C_1$-$C_5$ alkyl, $C_1$-$C_5$ hydroxy alkyl and $C_1$-$C_5$ amino alkyl;
X is optionally selected from chlorine or bromine;
wherein lipophilic moiety is selected from the group consisting of $C_{8-24}$ alkyl, mono-, di- and tri-unsaturated alkenyl,
said process comprising the following steps:
(a) coupling of compound of formula II with L-lysine derivatives in a polar aprotic solvent to obtain compound of formula III, followed by acid deprotection to obtain compound of formula IV,

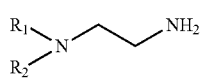

Formula II

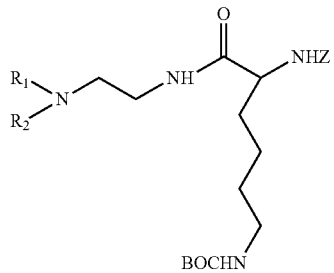

Formula III

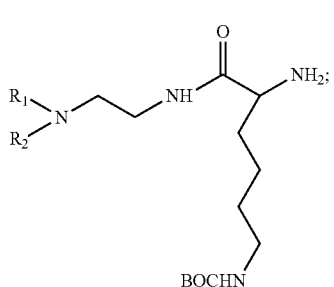

Formula IV;

(b) coupling of compound of formula IV obtained from step (a), with shikimic acid, quinic acid or mannose to obtain compound of formula V,

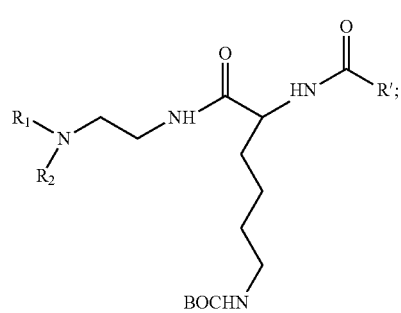

Formula V (c) deprotecting compound of formula V obtained from step (b) to obtain compound of formula VI, followed by guanidinylation of formula VI in aprotic solvent to obtain compound of formula VII,

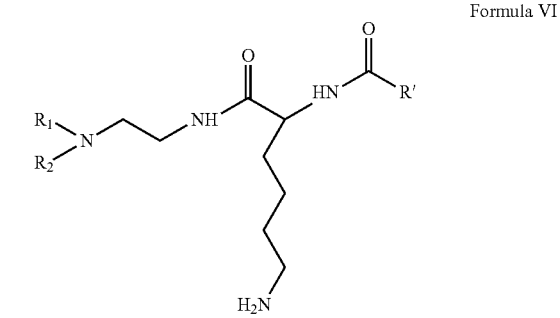

Formula VI

Formula VII

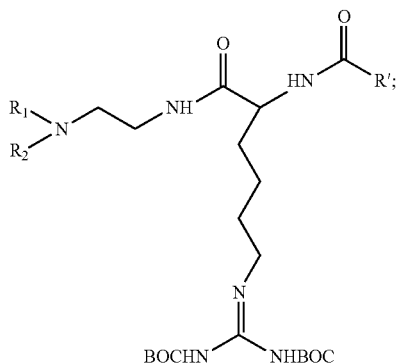

(d) quaternization of compound of formula VII obtained from step (c) with methyl iodide to obtain compound of formula VIII followed by base mediated deprotection in polar protic solvent to obtain compound of formula IX and finally extraction to obtain compound of formula I, Formula VIII

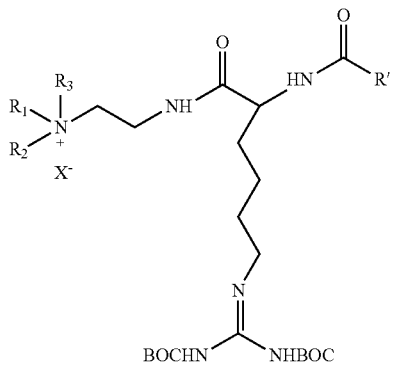

Formula IX

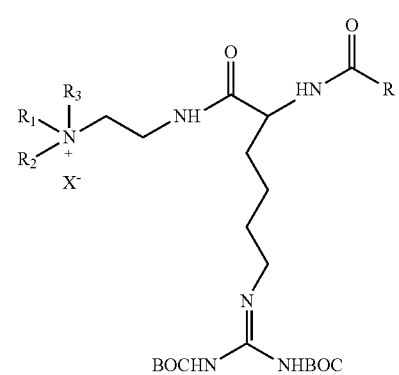

Formula I

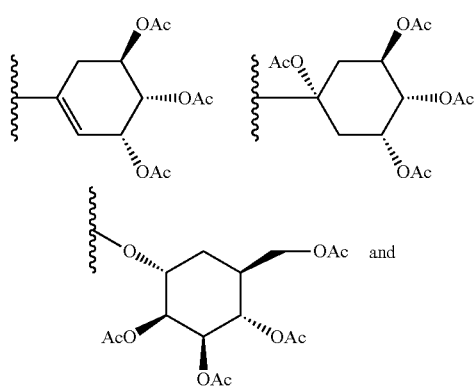

wherein R' is selected from the group consisting of shikimoyl, quinoyl, and mannosyl group,

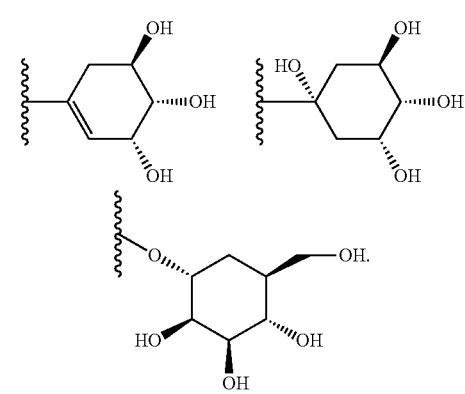

wherein R is selected from the group consisting of shikimoyl, quinoyl, and mannosyl group, 5. The process as claimed in claim 4, wherein the compound of formula II is having 8-24 carbon atoms.

6. The process as claimed in claim 4, wherein the polar aprotic solvent of step (a) and step (c) is selected from the group consisting of dichloromethane, dimethyl formamide, dimethylsulphoxide, pyridine, and triethyl amine.

7. The process as claimed in claim 4, wherein base is selected from the group consisting of potassium carbonate, lithium hydroxide, sodium hydroxide, sodium carbonate, potassium hydroxide, sodium methoxide and potassium methoxide.

8. The process as claimed in claim 4, wherein the polar protic solvent for base mediated deprotection in step (d) is selected from the group consisting of methanol, ethanol and mixture of water & methanol.

9. A formulation comprising the compound of formula I, a co-lipid, and a polyanionic compound along with physiologically acceptable additive.

10. The formulation as claimed in claim 9, wherein, the formulation further comprises helper lipids which is selected from the group consisting of cholesterol, phosphatidylethanolaine and phosphatidylglycerol.

11. The formulation as claimed in claim 9, wherein, the co lipid is selected from the group consisting of phosphatidylethanolamine, phosphatidylphosphocholine, neutral phosphatidyl ethanolamine, neutral phosphatidyl choline, phosphatidylglycerol, cholesterol, and 1,2-syn-dioleoyl-glycerolphosphatidylethanolamine (DOPE).

12. The formulation as claimed in claim 9, wherein, the molar ratio of compound of formula I to co lipid ranges from 1:1 to 3:1.

13. The formulation as claimed in claim 9, wherein, the polyanionic compound is selected from the group consisting of nucleic acid, a protein, an oligonucleotide, a peptide and a drug.

14. The formulation as claimed in claim 13, wherein, the nucleic acid is selected from the group consisting of plasmid, a ribonucleic acid, a ribosomal RNA, antisense polynucleotide of RNA or DNA, polynucleotide of genomic DNA, cDNA and mRNA.

15. The formulation as claimed in claim 9, wherein the formulation is administered via cutaneous, sub-cutaneous, intradermal, nasal, intravenous, intramuscular, intraperitonial and pulmonary route.

16. The formulation as claimed in claim 9, wherein the formulation is administered intracellularly in the range from 25 to 100 microliters.

17. The formulation as claimed in claim 9, wherein the formulation is administered to cells at a ratio 0.1 to 0.5 microgram of DNA to 50,000 cells.

18. The formulation as claimed in claim 9, wherein the range of compound of formula I is from 9.0 to 0.3 microgram and lipid to DNA ratio ranges from 0.3:1 to 9:1.

19. A method for producing an immune response, the method comprising administering the formulation of claim 9 with a polynucleotide wherein said polynucleotide encodes an immunogen to at least one mouse thereby generating at least one immunized mouse.

* * * * *